(12) United States Patent
Schottek et al.

(10) Patent No.: US 6,627,764 B1
(45) Date of Patent: Sep. 30, 2003

(54) TRANSITION METAL COMPOUND, LIGAND SYSTEM, CATALYST SYSTEM AND ITS USE FOR THE POLYMERIZATION OF OLEFINS

(75) Inventors: Jörg Schottek, Frankfurt (DE); Diana Schauer, Bruchköbel (DE); Roland Kratzer, Kriftel (DE)

(73) Assignee: Basell Polyolefine GmbH, Wesseling (DE)

( * ) Notice: Subject to any disclaimer, the term of this patent is extended or adjusted under 35 U.S.C. 154(b) by 97 days.

(21) Appl. No.: 09/614,121

(22) Filed: Jul. 11, 2000

(30) Foreign Application Priority Data

Jul. 31, 1999 (DE) .......................................... 199 36 185

(51) Int. Cl.⁷ .......................... C07F 17/00; B01J 31/00; C08F 4/44
(52) U.S. Cl. ............................... 556/11; 556/1; 556/12; 556/43; 556/53; 556/58; 526/160; 526/943; 502/103; 502/117
(58) Field of Search ................... 556/11, 12, 1, 556/43, 53, 58; 526/160, 943; 502/103, 117

(56) References Cited

U.S. PATENT DOCUMENTS

| | | | |
|---|---|---|---|
| 4,752,597 A | | 6/1988 | Turner .................. 502/104 |
| 5,017,714 A | | 5/1991 | Welborn, Jr. ............. 556/12 |
| 5,103,030 A | | 4/1992 | Rohrmann et al. ......... 556/12 |
| 5,278,264 A | * | 1/1994 | Spaleck et al. .......... 526/127 |
| 5,296,434 A | * | 3/1994 | Karl et al. ............. 502/117 |
| 5,304,614 A | | 4/1994 | Winter et al. ........... 526/127 |
| 5,532,396 A | * | 7/1996 | Winter et al. ............ 556/11 |
| 5,543,535 A | | 8/1996 | Lisowsky ................. 556/11 |
| 5,612,462 A | | 3/1997 | Lisowsky ................. 534/15 |
| 5,627,118 A | * | 5/1997 | Palackal et al. ......... 502/117 |
| 5,786,495 A | * | 7/1998 | Resconi et al. ........... 556/11 |

FOREIGN PATENT DOCUMENTS

| | | |
|---|---|---|
| EP | 129 368 | 12/1984 |
| EP | 320 762 | 6/1989 |
| EP | 416 815 | 3/1991 |
| EP | 537 686 | 4/1993 |
| EP | 659 757 | 6/1995 |
| EP | 669 340 | 8/1995 |

OTHER PUBLICATIONS

J.of Org.Chem., 232(1982)233–247, Wild et al.
J. Mol. Catalysis A:Chem., 128(1998) 272–287; Spaleck et al.
Angew. Chem, 107(1995), 1255–1283; Brintzinger et al.

* cited by examiner

*Primary Examiner*—Porfirio Nazario-Gonzalez
(74) *Attorney, Agent, or Firm*—Keil & Weinkauf

(57) ABSTRACT

Ligand systems containing indenyl structures, transition metal compounds of the metallocene type and catalyst systems comprising such transition metal compounds are described. The novel transition metal compounds can be used in the polymerization of olefins, in particular to give polyolefins having a low molar mass.

12 Claims, No Drawings

TRANSITION METAL COMPOUND, LIGAND SYSTEM, CATALYST SYSTEM AND ITS USE FOR THE POLYMERIZATION OF OLEFINS

The present invention relates to ligand systems, transition metal compounds, catalyst systems and their use in the polymerization of olefins.

Metallocenes can, if desired in combination with one or more cocatalysts, be used as catalyst components for the polymerization and copolymerization of olefins. In particular, halogen-containing metallocenes which can be converted, for example, by an aluminoxane into a polymerization-active cationic metallocene complex are used as catalyst precursors (EP-A-129368).

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al.; Angew. Chem., 107 (1995), 1255; H. H. Brintzinger et al., J. Organomet. Chem. 232 (1982), 233). They can be prepared, for example, by reacting cyclopentadienyl-metal compounds with halides of transition metals such as titanium, zirconium and hafnium.

A route which can be used for preparing isotactic polypropylene having a low molar mass is the addition of comparatively large amounts of hydrogen during the polymerization. This leads to processes which are difficult to control in engineering terms and to greatly increased costs.

It would therefore be desirable to have a cationic metallocene catalyst system in unsupported or supported form which gives the desired low molar masses of isotactic polypropylene in the presence of only small amounts of added hydrogen and also gives unaltered high activities and melting points.

Isotactic polypropylene having a low molar mass is of particular interest for film products.

EP-A-659757 and Spaleck et al., J. Mol. Catal. A: Chemical 1998, 128, 279–287, describe metallocene compounds which contain two differently substituted indenyl ligands. It is found that metallocene compounds in which there is no substituent in the 2 position on one of the indenyl substituents give isotactic polypropylene having low molar masses of 100,000–300,000 g/mol. However, a critical disadvantage of the compounds described there is that the polymerization activities in a heterogeneous polymerization are drastically reduced compared to a homogeneous polymerization. This leads to limited commercial utilization.

It is an object of the present invention to find metallocenes which, after conversion into the polymerization-active species, avoid the disadvantages of the prior art and display, in particular, a markedly increased polymerization activity with a heterogeneous polymerization procedure.

We have found that this object is achieved by metallocenes, in particular those which have specific substitutions on the indenyl ligand.

The present invention provides compounds of the formula (I),

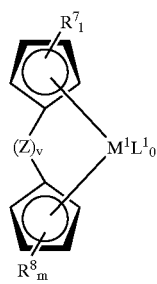

(I)

where $M^1$ is a metal of transition group III, IV, V or VI of the Periodic Table of the Elements, in particular Ti, Zr or Hf, $R^7$ are identical or different and are each a hydrogen atom or $Si(R^{12})_3$, where $R^{12}$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^7$ is a $C_1$–$C_{30}$-group such as $C_1$–$C_{25}$-alkyl, e.g. methyl, ethyl, tert-butyl, n-hexyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^7$ can be joined to one another so that the radicals $R^7$ and the atoms of the cyclopentadienyl ring which connect them form a $C_4$–$C_{24}$ ring system which may in turn be substituted, $R^8$ are identical or different and are each a hydrogen atom or $Si(R^{12})_3$, where $R^{12}$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^8$ is a $C_1$–$C_{30}$-group such as $C_1$–$C_{25}$-alkyl, e.g. methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl which together with the cyclopentadienyl ring form azapentalenes, thiopentalenes or phosphapentalenes, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^8$ can be joined to one another so that the radicals $R^8$ and the atoms of the cyclopentadienyl ring which connect them form a $C_4$–$C_{24}$ ring system which may in turn be substituted, l is 5 when v=0, and l is 4 when v=1, m is 5 when v=0, and m is 4 when v=1, $L^1$ can be identical or different and are each a hydrogen atom, a $C_1$–$C_{10}$-hydrocarbon group such as $C_1$–$C_{10}$-alkyl or $C_6$–$C_{10}$-aryl, a halogen atom, or $OR^9$, $SR^9$, $OSiR_3^9$, $SiR_3^9$, $PR_2^9$ or $NR_2^9$, where $R^9$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or $L^1$ is a toluenesulfonyl, trifluoroacetyl, trifluoroacetoxyl, trifluoromethanesulfonyl, nonafluorobutanesulfonyl or 2,2,2-trifluoroethanesulfonyl group, o is an integer from 1 to 4, preferably 2.

Z is a bridging structural element between the two cyclopentadienyl rings and v is 0 or 1.

Examples of Z are $MR^{10}R^{11}$ groups, where M is carbon or silicon and $R^{10}$ and $R^{11}$ are identical or different and are each a $C_1$–$C_{20}$-hydrocarbon-containing group such as $C_1$–$C_{10}$-alkyl, $C_6$–$C_{14}$-aryl, trialkylthionyl, in particular trimethylsilyl, triarylsilyl or an alkylarylsilyl group. Particularly preferred groups Z are $Si(Me)_2$, $Si(Ph)_2$, $Si(MeEt)$, $Si(PhMe)$, $Si(PhEt)$, $Si(Et)_2$, where Ph is substituted or unsubstituted phenyl and Et is ethyl. It is also possible for Z together with one or more radicals $R^7$ and/or $R^8$ to form a monocyclic or polycyclic ring system. In the abovementioned radicals, Ph is substituted or unsubstituted phenyl, Et is ethyl and Me is methyl.

Preference is given to bridged metallocene compounds of the formula (I), in particular those in which v is 1 and one or both cyclopentadienyl rings are substituted so that they form an indenyl ring. The indenyl ring is preferably substituted, particularly in the 2 position, 4 position, 2,4,5 positions, 2,4,6 positions, 2,4,7 positions or 2,4,5,6 positions, by $C_1$–$C_{20}$-groups such as $C_1$–$C_{18}$-alkyl or $C_6$–$C_{18}$-aryl, where two or more substituents of the indenyl ring may together form a ring system.

Particular preference is given to bridged metallocene compounds of the formula (II),

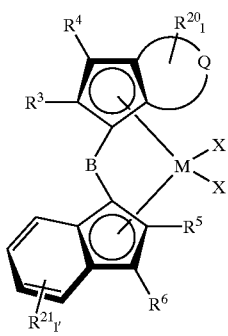

(II)

where

M is Ti, Zr or Hf, particularly preferably zirconium, $R^3$ is a hydrogen atom, a $C_1$–$C_{20}$-group, preferably $C_1$–$C_{18}$-alkyl such as methyl, ethyl, n-butyl, n-hexyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$ is a hydrogen atom, $R^6$ are identical or different and are each a hydrogen atom, a $C_1$–$C_{20}$-group, preferably $C_1$–$C_{18}$-alkyl such as methyl, ethyl, n-butyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^{20}$, $R^{21}$ are identical or different and are each a hydrogen atom, a halogen atom or a $C_1$–$C_{20}$-group, preferably a linear or branched $C_1$–$C_{18}$-alkyl group such as methyl, ethyl, tert-butyl, cyclohexyl or octyl, $C_2$–$C_{10}$-alkenyl, $C_3$–$C_{15}$-alkylalkenyl, a $C_6$–$C_{18}$-aryl group which may be substituted or unsubstituted, in particular phenyl, tolyl, xylyl, tert-butylphenyl, ethylphenyl, naphthyl, acenaphthyl, phenanthrenyl or anthracenyl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and two radicals $R^{20}$ or $R^{21}$ may form a monocyclic or polycyclic ring system which may in turn be substituted or unsubstituted, X is a halogen atom, in particular chlorine, Q is a $C_4$–$C_{24}$-aryl ring system which may in turn bear a group $R^{20}$ as substituent or a heteroaryl which together with the cyclopentadienyl ring forms an azapentalene, thiopentalene or phosphapentalene which may in turn bear a group $R^{20}$ as substituent, l, l' are identical or different and are each an integer from zero to 4, preferably 1 or 2, particularly preferably 1, B is a bridging structural element between the two indenyl radicals.

Examples of B are $M^3R^{13}R^{14}$ groups, where $M^3$ is silicon and $R^{13}$ and $R^{14}$ are identical or different and are each a $C_1$–$C_{20}$-hydrocarbon-containing group such as $C_1$–$C_{10}$-alkyl, $C_6$–$C_{14}$-aryl, trialkylsilyl, in particular trimethylsilyl, triarylsilyl or an alkylarylsilyl group. Particularly preferred groups B are $Si(Me)_2$, $Si(Ph)_2$, $Si(MeEt)$, $Si(PhMe)$, $Si(PHEt)$, $Si(Et)_2$, where Ph is substituted or unsubstituted phenyl and Et is ethyl. It is also possible for B together with one or more radicals $R^7$ or $R^8$ to form a monocyclic or polycyclic ring system.

Very particular preference is given to bridged metallocene compounds of the formula (II) in which M is zirconium, $R^3$ are identical or different and are each a hydrogen atom or a $C_1$–$C_{12}$-alkyl group, preferably an alkyl group such as methyl, ethyl, n-butyl, n-hexyl or octyl, particularly preferably methyl or ethyl, $R^5$ is a hydrogen atom, $R^4$, $R^6$ are hydrogen atoms, $R^{20}$, $R^{21}$ are identical or different and are each a hydrogen atom, a halogen atom or a $C_1$–$C_{20}$-group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group which may be substituted or unsubstituted, in particular phenyl, tolyl, xylyl, tert-butylphenyl, ethylphenyl, naphthyl, acenaphthyl, phenanthrenyl or anthracenyl, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, X is chlorine, Q is a $C_4$-aryl which together with the cyclopentadienyl ring forms an indenyl system which may in turn bear a group $R^{20}$ as substituent, or a heteroaryl which together with the cyclopentadienyl ring forms an azapentalene, thiopentalene or phosphapentalene which may in turn bear a group $R^{20}$ as substituent, l, l' are identical or different and are each an integer from zero to 4, preferably 1 or 2, particularly preferably 1, B is a bridging structural element between the two indenyl radicals and is preferably $Si(Me)_2$, $Si(Ph)_2$, $Si(Et)_2$, $Si(MePh)$.

The invention further provides ligand systems of the formula (IIa) in which the radicals have the same meaning as in formula (II)

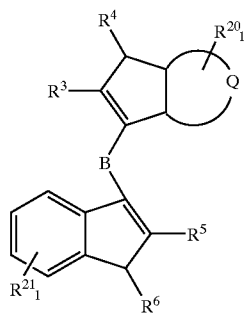

The novel metallocenes of the formulae I and II give isotactic polypropylene having a low molar mass (50,000–300,000 g/mol) without introduction of hydrogen during the polymerization, unlike the corresponding symmetrically or unsymmetrically substituted metallocenes which are substituted in position 2. For application which demand precisely set molar masses (defined MFI), it is possible to add small amounts of hydrogen to the novel metallocenes of the formulae I and II.

Instead of the pure, chiral bridged metallocene compounds of the formula (II) pseudo(rac), the catalyst can also be produced using mixtures of the metallocenes of the formula (II) and the corresponding pseudomeso metallocenes of the formula (IIb).

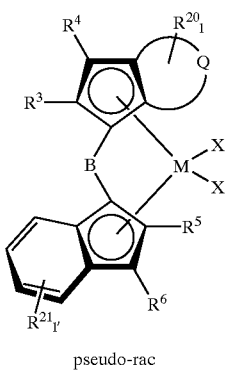

pseudo-rac

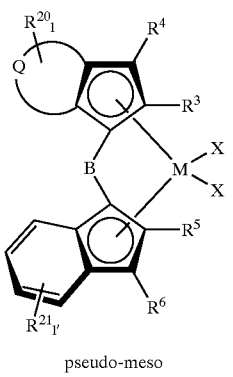

pseudo-meso

Illustrative, but not restrictive, examples of the metallocenes of the present invention are:

dimethylsilanediyl(2-methyl-4-(4'-tert-butylphenyl)indenyl)-(1-indenyl)zirconium dichloride
dimethylsilanediyl(2-methyl-4-(4'-tert-butylphenyl)indenyl)-(1-indenyl)hafnium dichloride
dimethylsilanediyl(2-methyl-4-(4'-tert-butylphenyl)indenyl)-(1-indenyl)titanium dichloride
dimethylsilanediyl(2-methyl-4-(4'-methylphenyl)indenyl)-(1-indenyl)zirconium dichloride
dimethylsilanediyl(2-methyl-4-(4'-ethylphenyl)indenyl)-(1-indenyl)zirconium dichloride
dimethylsilanediyl(2-methyl-4-(4'-n-propylphenyl)indenyl)-(1-indenyl)zirconium dichloride
dimethylsilanediyl(2-methyl-4-(4'-isopropylphenyl)indenyl)-(1-indenyl)zirconium dichloride
dimethylsilanediyl(2-methyl-4-(4'-n-butylphenyl)indenyl)-(1-indenyl)zirconium dichloride
dimethylsilanediyl(2-methyl-4-(4'-hexylphenyl)indenyl)-(1-indenyl)zirconium dichloride
dimethylsilanediyl(2-methyl-4-(4'-sec-butylphenyl)indenyl)-(1-indenyl)zirconium dichloride
dimethylsilanediyl(9-fluorenyl)-(1-indenyl)zirconium dichloride
dimethylsilanediyl(9-(3-methyl)fluorenyl)-(1-indenyl)zirconium dichloride
dimethylsilanediyl(9-(2-tert-butyl)fluorenyl)-(1-indenyl)zirconium dichloride
dimethylsilanediyl(9-(2,7-di-tert-butyl)fluorenyl)(1-indenyl)zirconium dichloride
dimethylsilanediyl(9-(2,7-diphenyl)fluorenyl)(1-indenyl)zirconium dichloride
dimethylsilanediyl(4-naphthylindenyl)(2-methyl-4-(4'-tert-butylphenyl)indenyl)zirconium dichloride
dimethylsilanediyl(2-methylbenzoindenyl)(1-indenyl)zirconium dichloride
dimethylsilanediyl(2-methylindenyl)(1-indenyl)zirconium dichloride
dimethylsilanediyl(2-methyl-4-(1-naphthyl)indenyl)(1-indenyl)zirconium dichloride
dimethylsilanediyl(2-methyl-4-(2-naphthyl)(1-indenyl)zirconium dichloride
dimethylsilanediyl(2-methyl-4-t-butyl-indenyl)(1-indenyl)zirconium dichloride
dimethylsilanediyl(2-methyl-4-ethylindenyl)(1-indenyl)zirconium dichloride
dimethylsilanediyl(2-methyl-4-acenaphthindenyl)(1-indenyl)zirconium dichloride
dimethylsilanediyl(2-ethylindenyl)(1-indenyl)zirconium dichloride
dimethylsilanediyl(2-ethyl-4-ethylindenyl)(1-indenyl)zirconium dichloride
dimethylsilanediyl(2-ethyl-4-phenylindenyl)(1-indenyl)zirconium dichloride
dimethylsilanediyl(2-methyl-4-(tert-butylphenylindenyl)(1-indenyl)zirconium dichloride
dimethylsilanediyl(2-methyl-4-(4-methylphenylindenyl)(1-indenyl)-zirconium dichloride
dimethylsilanediyl(2-methyl-4-(4-ethylphenylindenyl)(1-indenyl)zirconium dichloride
dimethylsilanediyl(2-methyl-4-(4-trifluoromethylphenylindenyl)(1-indenyl)zirconium dichloride
dimethylsilanediyl(2-methyl-4-(4-methoxyphenylindenyl)(1-indenyl)zirconium dichloride
dimethylsilanediyl(2-ethyl-4-(4-tert-butylphenylindenyl)(1-indenyl)zirconium dichloride
dimethylsilanediyl(2-ethyl-4-(4-methylphenylindenyl)(1-indenyl)zirconium dichloride dimethylsilanediyl(2-ethyl-4-(4-ethylphenylindenyl)(1-indenyl)zirconium dichloride dimethylsilanediyl(2-ethyl-4-(4-trifluoromethylphenylindenyl)(1-indenyl)zirconium dichloride dimethylsilanediyl(2-ethyl-4-(4-methoxyphenylindenyl)(1-indenyl)zirconium dichloride dimethylsilanediyl(2-ethyl-4-(4-ethylphenylindenyl)(1-indenyl)diethylzirconium dimethylsilanediyl(2-methyl-4-(4'-hexylphenyl)indenyl)(1-indenyl)zirconium dichloride dimethylsilanediyl(2-methyl-4-(4'-sec-butylphenyl)indenyl)(1-indenyl)zirconium dichloride dimethylsilanediyl(2-ethyl-4-phenyl)indenyl)(1-indenyl)zirconium dichloride dimethylsilanediyl(2-ethyl-4-(4'-methylphenyl)indenyl)(1-indenyl)zirconium dichloride dimethylsilanediyl(2-ethyl-4-(4'-ethylphenyl)indenyl)(1-indenyl)zirconium dichloride dimethylsilanediyl(2-ethyl-4-(4'-n-propylphenyl)indenyl)(1-indenyl)zirconium dichloride dimethylsilanediyl(2-ethyl-4-(4'-isopropylphenyl)indenyl)(1-indenyl)zirconium dichloride dimethylsilanediyl(2-ethyl-4-(4'-n-butylphenyl)indenyl)(1-indenyl)zirconium dichloride dimethylsilanediyl(2-ethyl-4-(4'-hexylphenyl)indenyl)(1-indenyl)zirconium dichloride dimethylsilanediyl(2-ethyl-4-(4'-pentylphenyl)indenyl)(1-indenyl)zirconium dichloride dimethylsilanediyl(2-ethyl-4-(4'-cyclohexylphenyl)indenyl)(1-indenyl)zirconium dichloride dimethylsilanediyl(2-ethyl-4-(4'-sec-butylphenyl)indenyl)(1-indenyl)zirconium dichloride dimethylsilanediyl(2-ethyl-4-(4'-tert-butylphenyl)indenyl)(1-indenyl)zirconium dichloride dimethylsilanediyl(2-n-propyl-4-phenyl)indenyl)(1-indenyl)zirconium dichloride dimethylsilanediyl(2-n-propyl-4-(4'-methylphenyl)indenyl)(1-indenyl)zirconium dichloride dimethylsilanediyl(2-n-propyl-4-(4'-ethylphenyl)indenyl)(1-indenyl)zirconium dichloride dimethylsilanediyl(2-n-propyl-4-(4'-n-propylphenyl)indenyl)(1-indenyl)zirconium dichloride dimethylsilanediyl(2-n-propyl-4-(4'-isopropylphenyl)indenyl)(1-indenyl)zirconium dichloride dimethylsilanediyl(2-n-propyl-4-(4'-n-butylphenyl)indenyl)(1-indenyl)zirconium dichloride dimethylsilanediyl(2-n-propyl-4-(4'-hexylphenyl)indenyl)(1-indenyl)zirconium dichloride dimethylsilanediyl(2-n-propyl-4-(4'-cyclohexylphenyl)indenyl)(1-indenyl)zirconium dichloride dimethylsilanediyl(2-n-propyl-4-(4'-sec-butylphenyl)indenyl)(1-indenyl)zirconium dichloride dimethylsilanediyl(2-n-propyl-4-(4'-tert-butylphenyl)indenyl)(1-indenyl)zirconium dichloride dimethylsilanediyl(2-n-butyl-4-phenyl)indenyl)(1-indenyl)zirconium dichloride dimethylsilanediyl(2-n-butyl-4-(4'-methylphenyl)indenyl)(1-indenyl)zirconium dichloride dimethylsilanediyl(2-n-butyl-4-(4'-ethylphenyl)indenyl)(1-indenyl)zirconium dichloride dimethylsilanediyl(2-n-butyl-4-(4'-n-propylphenyl)indenyl)(1-indenyl)zirconium dichloride dimethylsilanediyl(2-n-butyl-4-(4'-isopropylphenyl)indenyl)(1-indenyl)zirconium dichloride dimethylsilanediyl(2-n-butyl-4-(4'-n-butylphenyl)indenyl)(1-indenyl)zirconium dichloride dimethylsilanediyl(2-n-butyl-4-(4'-hexylphenyl)indenyl)(1-indenyl)zirconium dichloride dimethylsilanediyl(2-n-butyl-4-(4'-cyclohexylphenyl)indenyl)(1-indenyl)zirconium dichloride dimethylsilanediyl(2-n-butyl-4-(4'-sec-butylphenyl)indenyl)(1-indenyl)zirconium dichloride dimethylsilanediyl(2-n-butyl-4-(4'-tert-butylphenyl)indenyl)(1-indenyl)zirconium dichloride dimethylsilanediyl(2-hexyl-4-phenyl)indenyl)(1-indenyl)zirconium dichloride dimethylsilanediyl(2-hexyl-4-(4'-methylphenyl)indenyl)(1-indenyl)zirconium dichloride dimethylsilanediyl(2-hexyl-4-(4'-ethylphenyl)indenyl)(1-indenyl)zirconium dichloride dimethylsilanediyl(2-hexyl-4-(4'-n-propylphenyl)indenyl)(1-indenyl)zirconium dichloride dimethylsilanediyl(2-hexyl-4-(4'-iso-propylphenyl)indenyl)(1-indenyl)zirconium dichloride dimethylsilanediyl(2-hexyl-4-(4'-n-butylphenyl)indenyl)(1-indenyl)zirconium dichloride dimethylsilanediyl(2-hexyl-4-(4'-hexylphenyl)indenyl)(1-indenyl)zirconium dichloride dimethylsilanediyl(2-hexyl-4-(4'-cyclohexylphenyl)indenyl)(1-indenyl)zirconium dichloride dimethylsilanediyl(2-hexyl-4-(4'-sec-butylphenyl)indenyl)(1-indenyl)zirconium dichloride dimethylsilanediyl(2-hexyl-4-(4'-tert-butylphenyl)indenyl)(1-indenyl)zirconium dichloride dimethylsilanediyl(2-methylazapentalene)(1-indenyl)zirconium dichloride dimethylsilanediyl(2-methylthiapentalene)(1-indenyl)zirconium dichloride dimethylsilanediyl(2-methylphosphapentalene)(1-indenyl)zirconium dichloride dimethylsilanediyl(2-ethylazapentalene)(1-indenyl)zirconium dichloride dimethylsilanediyl(2-methyl-4-(4'-tert-butylphenyl)indenyl)-(4-(4'-tert-butylphenyl)indenyl)zirconium dichloride dimethylsilanediyl(2-methyl-4-(4'-tert-butylphenyl)indenyl)-(4-(4'-tert-butylphenyl)indenyl)hafnium dichloride dimethylsilanediyl(2-methyl-4-(4'-tert-butylphenyl)indenyl)-(4-(4'-tert-butylphenyl)indenyl)titanium dichloride dimethylsilanediyl(2-methyl-4-(4'-methylphenyl)indenyl)-(4-(4'-tert-butylphenyl)indenyl)zirconium dichloride dimethylsilanediyl(2-methyl-4-(4'-ethylphenyl)indenyl)-(4-(4'-tert-butylphenyl)indenyl)zirconium dichloride dimethylsilanediyl(2-methyl-4-(4'-n-propylphenyl)indenyl)-(4-(4'-tert-butylphenyl)indenyl)zirconium dichloride dimethylsilanediyl(2-methyl-4-(4'-isopropylphenyl)indenyl)-(4-(4'-tert-butylphenyl)indenyl)zirconium dichloride dimethylsilanediyl(2-methyl-4-(4'-n-butylphenyl)indenyl)-(4-(4'-tert-butylphenyl)indenyl)zirconium dichloride dimethylsilanediyl(2-methyl-4-(4'-hexylphenyl)indenyl)-(4-(4'-tert-butylphenyl)indenyl)zirconium dichloride dimethylsilanediyl(2-methyl-4-(4'-sec-butylphenyl)indenyl)-(4-(4'-tert-butylphenyl)indenyl)zirconium dichloride dimethylsilanediyl(4-naphthylindenyl)(2-methyl-4-(4'-tert-butylphenyl)indenyl)zirconium dichloride dimethylsilanediyl(2-methylbenzoindenyl)-(4-(4'-tert-butylphenyl)indenyl)zirconium dichloride dimethylsilanediyl(2-methylindenyl)(4-(4'-tert-butylphenyl)indenyl)zirconium dichloride dimethylsilanediyl(2-methyl-4-(1-naphthyl)indenyl)-(4-(4'-tert-butylphenyl)indenyl)zirconium dichloride dimethylsilanediyl(2-methyl-4-(2-naphthyl)(4-(4'-tert-butylphenyl)indenyl)zirconium dichloride dimethylsilanediyl(2-methyl-4-t-butylindenyl)-(4-(4'-tert-butylphenyl)indenyl)zirconium dichloride dimethylsilanediyl(2-methyl-4-ethylindenyl)-(4-(4'-tert-butylphenyl)indenyl)zirconium dichloride dimethylsilanediyl(2-methyl-4-acenaphthindenyl)-(4-(4'-tert-butylphenyl)-indenyl)zirconium dichloride dimethylsilanediyl(2-ethylindenyl)(4-(4'-tert-butylphenyl)indenyl)zirconium dichloride dimethylsilanediyl(2-ethyl-4-ethylindenyl)(4-(4'-tert-butylphenyl)indenyl)zirconium dichloride dimethylsilanediyl(2-ethyl-4-phenylindenyl)-(4-(4'-tert-butylphenyl)indenyl)zirconium dichloride dimethylsilanediyl(2-methyl-4-(tert-butylphenylindenyl)-(4-(4'-tert-butylphenyl)indenyl)zirconium dichloride dimethylsilanediyl(2-methyl-4-(4-methylphenylindenyl)-(4-(4'-tert-butylphenyl)indenyl)zirconium dichloride dimethylsilanediyl(2-methyl-4-(4-ethylphenylindenyl)-(4-(4'-tert-butylphenyl)indenyl)zirconium dichloride dimethylsilanediyl(2-methyl-4-(4-trifluoromethylphenylindenyl)-(4-(4'-tert-butylphenyl)indenyl)zirconium dichloride dimethylsilanediyl(2-methyl-4-(4-methoxyphenylindenyl)-(4-(4'-tert-butylphenyl)indenyl)zirconium dichloride dimethylsilanediyl(2-ethyl-4-(4-tert-butylphenylindenyl)-(4-(4'-tert-butylphenyl)indenyl)zirconium dichloride dimethylsilanediyl(2-ethyl-4-(4-methylphenylindenyl)-(4-(4'-tert-butylphenyl)indenyl)zirconium dichloride dimethylsilanediyl(2-ethyl-4-(4-ethylphenylindenyl)-(4-(4'-tert-butylphenyl)indenyl)zirconium dichloride dimethylsilanediyl(2-ethyl-4-(4-trifluoromethylphenylindenyl)-(4-(4'-tert-butylphenyl)indenyl)zirconium dichloride dimethylsilanediyl(2-ethyl-4-(4-methoxyphenylindenyl)-(4-(4'-tert-butylphenyl)indenyl)zirconium dichloride dimethylsilanediyl(2-ethyl-4-(4-ethylphenylindenyl)-(4-(4'-tert-butylphenyl)indenyl)diethylzirconium dimethylsilanediyl(2-ethyl-4-phenyl)indenyl)-(4-(4'-tert-butylphenyl)indenyl)zirconium dichloride dimethylsilanediyl(2-ethyl-4-(4'-methylphenyl)indenyl)-(4-(4'-tert-butylphenyl)indenyl)zirconium dichloride dimethylsilanediyl(2-ethyl-4-(4'-ethylphenyl)indenyl)-(4-(4'-tert-butylphenyl)indenyl)zirconium dichloride dimethylsilanediyl(2-ethyl-4-(4'-n-propylphenyl)indenyl)-(4-(4'-tert-butylphenyl)indenyl)zirconium dichloride dimethylsilanediyl(2-ethyl-4-(4'-isopropylphenyl)indenyl)-(4-(4'-tert-butylphenyl)-indenyl)zirconium dichloride dimethylsilanediyl(2-ethyl-4-(4'-n-butylphenyl)indenyl)-(4-(4'-tert-butylphenyl)indenyl)zirconium dichloride dimethylsilanediyl(2-ethyl-4-(4'-hexylphenyl)indenyl)-(4-(4'-tert-butylphenyl)indenyl)zirconium dichloride dimethylsilanediyl(2-ethyl-4-(4'-pentylphenyl)indenyl)-(4-(4'-tert-butylphenyl)indenyl)zirconium dichloride dimethylsilanediyl(2-ethyl-4-(4'-cyclohexylphenyl)indenyl)-(4-(4'-tert-butylphenyl)indenyl)zirconium dichloride dimethylsilanediyl(2-ethyl-4-(4'-sec-butylphenyl)indenyl)-(4-(4'-tert-butylphenyl)indenyl)zirconium dichloride dimethylsilanediyl(2-ethyl-4-(4'-tert-butylphenyl)indenyl)-(4-(4'-tert-butylphenyl)indenyl)zirconium dichloride dimethylsilanediyl(2-n-propyl-4-phenyl)indenyl)-(4-(4'-tert-butylphenyl)indenyl)zirconium dichloride dimethylsilanediyl(2-n-propyl-4-(4'-methylphenyl)indenyl)-(4-(4'-tert-butylphenyl)indenyl)zirconium dichloride dimethylsilanediyl(2-n-propyl-4-(4'-ethylphenyl)indenyl)-(4-(4'-tert-butylphenyl)indenyl)zirconium dichloride dimethylsilanediyl(2-n-propyl-4-(4'-n-propylphenyl)indenyl)-(4-(4'-tert-butylphenyl)indenyl)zirconium dichloride dimethylsilanediyl(2-n-propyl-4-(4'-isopropylphenyl)indenyl)-(4-(4'-tert-butylphenyl)indenyl)zirconium dichloride dimethylsilanediyl(2-n-propyl-4-(4'-n-butylphenyl)indenyl)-(4-(4'-tert-butylphenyl)indenyl)zirconium dichloride dimethylsilanediyl(2-n-propyl-4-(4'-hexylphenyl)indenyl)-(4-(4'-tert-butylphenyl)indenyl)zirconium dichloride dimethylsilanediyl(2-n-propyl-4-(4'-cyclohexylphenyl)indenyl)-(4-(4'-tert-butylphenyl)indenyl)zirconium dichloride dimethylsilanediyl(2-n-propyl-4-(4'-sec-butylphenyl)indenyl)-(4-(4'-tert-butylphenyl)indenyl)zirconium dichloride dimethylsilanediyl(2-n-propyl-4-(4'-tert-butylphenyl)indenyl)-(4-(4'-tert-butylphenyl)indenyl)zirconium dichloride dimethylsilanediyl(2-n-butyl-4-phenyl)indenyl)-(4-(4'-tert-butylphenyl)indenyl)zirconium dichloride dimethylsilanediyl(2-n-butyl-4-(4'-methylphenyl)indenyl)-(4-(4'-tert-butylphenyl)indenyl)zirconium dichloride dimethylsilanediyl(2-n-butyl-4-(4'-ethylphenyl)indenyl)-(4-(4'-tert-butylphenyl)indenyl)zirconium dichloride dimethylsilanediyl(2-n-butyl-4-(4'-n-propylphenyl)indenyl)-(4-(4'-tert-butylphenyl)indenyl)zirconium dichloride dimethylsilanediyl(2-n-butyl-4-(4'-isopropylphenyl)indenyl)-(4-(4'-tert-butylphenyl)indenyl)zirconium dichloride dimethylsilanediyl(2-n-butyl-4-(4'-n-butylphenyl)indenyl)-(4-(4'-tert-butylphenyl)indenyl)zirconium dichloride dimethylsilanediyl(2-n-butyl-4-(4'-hexylphenyl)indenyl)-(4-(4'-tert-butylphenyl)indenyl)zirconium dichloride
dimethylsilanediyl(2-n-butyl-4-(4'-cyclohexylphenyl)indenyl)-(4-(4'-tert-butylphenyl)indenyl)zirconium dichloride
dimethylsilanediyl(2-n-butyl-4-(4'-sec-butylphenyl)indenyl)-(4-(4'-tert-butylphenyl)indenyl)zirconium dichloride
dimethylsilanediyl(2-n-butyl-4-(4'-tert-butylphenyl)indenyl)-(4-(4'-tert-butylphenyl)indenyl)zirconium dichloride
dimethylsilanediyl(2-hexyl-4-phenyl)indenyl)-(4-(4'-tert-butylphenyl)indenyl)zirconium dichloride
dimethylsilanediyl(2-hexyl-4-(4'-methylphenyl)indenyl)-(4-(4'-tert-butylphenyl)indenyl)zirconium dichloride
dimethylsilanediyl(2-hexyl-4-(4'-ethylphenyl)indenyl)-(4-(4'-tert-butylphenyl)indenyl)zirconium dichloride
dimethylsilanediyl(2-hexyl-4-(4'-n-propylphenyl)indenyl)-(4-(4'-tert-butylphenyl)indenyl)zirconium dichloride
dimethylsilanediyl(2-hexyl-4-(4'-iso-propylphenyl)indenyl)-(4-(4'-tert-butylphenyl)indenyl)zirconium dichloride
dimethylsilanediyl(2-hexyl-4-(4'-n-butylphenyl)indenyl)-(4-(4'-tert-butylphenyl)indenyl)zirconium dichloride
dimethylsilanediyl(2-hexyl-4-(4'-hexylphenyl)indenyl)-(4-(4'-tert-butylphenyl)indenyl)zirconium dichloride
dimethylsilanediyl(2-hexyl-4-(4'-cyclohexylphenyl)indenyl)-(4-(4'-tert-butylphenyl)indenyl)zirconium dichloride
dimethylsilanediyl(2-hexyl-4-(4'-sec-butylphenyl)indenyl)-(4-(4'-tert-butylphenyl)indenyl)zirconium dichloride
dimethylsilanediyl(2-hexyl-4-(4'-tert-butylphenyl)indenyl)-(4-(4'-tert-butylphenyl)indenyl)zirconium dichloride
dimethylsilanediyl(2-methylazapentalene)-(4-(4'-tert-butylphenyl)indenyl)zirconium dichloride
dimethylsilanediyl(2-methylthiapentalene)-(4-(4'-tert-butylphenyl)indenyl)zirconium dichloride
dimethylsilanediyl(2-methyl-phosphapentalene)-(4-(4'-tert-butylphenyl)indenyl)zirconium dichloride
dimethylsilanediyl(2-ethylazapentalene)-(4-(4'-tert-butylphenyl)indenyl)zirconium dichloride
dimethylsilanediyl(2-ethylthiapentalene)-(4-(4'-tert-butylphenyl)indenyl)zirconium dichloride
dimethylsilanediyl(2-ethylphosphapentalene)-(4-(4'-tert-butylphenyl)indenyl)zirconium dichloride
dimethylsilanediyl(2-methyl-4-(4'-tert-butylphenyl)indenyl)-(4-phenyl)indenylzirconium dichloride
dimethylsilanediyl(2-methyl-4-(4'-tert-butylphenyl)indenyl)-(4-phenyl)indenylhafnium dichloride
dimethylsilanediyl(2-methyl-4-(4'-tert-butylphenyl)indenyl)-(4-phenyl)indenyltitanium dichloride
dimethylsilanediyl(2-methyl-4-(4'-methylphenyl)indenyl)-(4-phenyl)indenyl-zirconium dichloride
dimethylsilanediyl(2-methyl-4-(4'-ethylphenyl)indenyl)-(4-phenyl)indenylzirconium dichloride
dimethylsilanediyl(2-methyl-4-(4'-n-propylphenyl)indenyl)-(4-phenyl)indenyl)zirconium dichloride
dimethylsilanediyl(2-methyl-4-(4'-isopropylphenyl)indenyl)-(4-phenyl)indenylzirconium dichloride
dimethylsilanediyl(2-methyl-4-(4'-n-butylphenyl)indenyl)-(4-phenyl)indenylzirconium dichloride
dimethylsilanediyl(2-methyl-4-(4'-hexylphenyl)indenyl)-(4-phenyl)indenyl)zirconium dichloride
dimethylsilanediyl(2-methyl-4-(4'-sec-butylphenyl)indenyl)-(4-phenyl)indenylzirconium dichloride
dimethylsilanediyl(9-fluorenyl)-(4-phenyl)indenyl zirconium dichloride
dimethylsilanediyl(9-(2,7-di-tert-butyl)fluorenyl)-(4-phenyl)indenylzirconium dichloride
dimethylsilanediyl(2-methylbenzoindenyl)(4-phenyl)indenyl)zirconium dichloride
dimethylsilanediyl(2-methylindenyl)(4-phenyl)indenyl)zirconium dichloride
dimethylsilanediyl(2-methyl-4-(1-naphthyl)indenyl)-(4-phenyl)indenyl)zirconium dichloride
dimethylsilanediyl(2-methyl-4-(2-naphthyl)(4-phenyl)indenyl)zirconium dichloride
dimethylsilanediyl(2-methyl-4-t-butylindenyl)-(4-phenyl)indenyl)zirconium dichloride
dimethylsilanediyl(2-methyl-4-ethylindenyl)-(4-phenyl)indenyl)zirconium dichloride
dimethylsilanediyl(2-methyl-4-acenaphthindenyl)-(4-phenyl)indenyl)zirconium dichloride
dimethylsilanediyl(2-ethylindenyl)(4-phenyl)indenyl zirconium dichloride
dimethylsilanediyl(2-ethyl-4-ethylindenyl)-(4-phenyl)indenyl)zirconium dichloride
dimethylsilanediyl(2-ethyl-4-phenylindenyl)-(4-phenyl)indenyl)zirconium dichloride
dimethylsilanediyl(2-methyl-4-(tert-butylphenylindenyl)-(4-phenyl)indenyl)zirconium dichloride
dimethylsilanediyl(2-methyl-4-(4-methylphenylindenyl)-(4-phenyl)indenyl)zirconium dichloride
dimethylsilanediyl(2-methyl-4-(4-ethylphenylindenyl)-(4-phenyl)indenyl)zirconium dichloride
dimethylsilanediyl(2-methyl-4-(4-trifluoromethylphenylindenyl)-(4-phenyl)indenylzirconium dichloride
dimethylsilanediyl(2-methyl-4-(4-methoxyphenylindenyl)-(4-phenyl)indenyl)zirconium dichloride
dimethylsilanediyl(2-ethyl-4-(4-tert-butylphenylindenyl)-(4-phenyl)indenyl)zirconium dichloride
dimethylsilanediyl(2-ethyl-4-(4-methylphenylindenyl)-(4-phenyl)indenyl)zirconium dichloride
dimethylsilanediyl(2-ethyl-4-(4-ethylphenylindenyl)-(4-phenyl)indenyl)zirconium dichloride
dimethylsilanediyl(2-ethyl-4-(4-trifluoromethylphenylindenyl)-(4-phenyl)indenylzirconium dichloride
dimethylsilanediyl(2-ethyl-4-(4-methoxyphenylindenyl)-(4-phenyl)indenyl)zirconium dichloride
dimethylsilanediyl(2-ethyl-4-phenyl)indenyl)-(4-phenyl)indenyl)zirconium dichloride
dimethylsilanediyl(2-ethyl-4-(4'-methylphenyl)indenyl)-(4-phenyl)indenyl)zirconium dichloride
dimethylsilanediyl(2-ethyl-4-(4'-ethylphenyl)indenyl)-(4-phenyl)indenyl)zirconium dichloride
dimethylsilanediyl(2-ethyl-4-(4'-n-propylphenyl)indenyl)-(4-phenyl)indenyl)zirconium dichloride dimethylsilanediyl(2-ethyl-4-(4'-isopropylphenyl)
  indenyl)-(4-phenyl)indenylzirconium dichloride
dimethylsilanediyl(2-ethyl-4-(4'-n-butylphenyl)indenyl)-
  (4-phenyl)indenyl)zirconium dichloride
dimethylsilanediyl(2-ethyl-4-(4'-hexylphenyl)indenyl)-
  (4-phenyl)indenyl)zirconium dichloride
dimethylsilanediyl(2-ethyl-4-(4'-pentylphenyl)indenyl)-
  (4-phenyl)indenyl)zirconium dichloride
dimethylsilanediyl(2-ethyl-4-(4'-cyclohexylphenyl)
  indenyl)-(4-phenyl)indenylzirconium dichloride
dimethylsilanediyl(2-ethyl-4-(4'-sec-butylphenyl)
  indenyl)-(4-phenyl)indenylzirconium dichloride
dimethylsilanediyl(2-ethyl-4-(4'-tert-butylphenyl)
  indenyl)-(4-phenyl)indenyl)zirconium dichloride
dimethylsilanediyl(2-n-propyl-4-phenyl)indenyl)-(4-
  phenyl)indenyl)zirconium dichloride
dimethylsilanediyl(2-n-propyl-4-(4'-methylphenyl)
  indenyl)-(4-phenyl)indenylzirconium dichloride
dimethylsilanediyl(2-n-propyl-4-(4'-ethylphenyl)
  indenyl)-(4-phenyl)indenylzirconium dichloride
dimethylsilanediyl(2-n-propyl-4-(4'-n-propylphenyl)
  indenyl)-(4-phenyl)indenylzirconium dichloride
dimethylsilanediyl(2-n-propyl-4-(4'-isopropylphenyl)
  indenyl)-(4-phenyl)indenylzirconium dichloride
dimethylsilanediyl(2-n-propyl-4-(4'-n-butylphenyl)
  indenyl)-(4-phenyl)indenylzirconium dichloride
dimethylsilanediyl(2-n-propyl-4-(4'-hexylphenyl)
  indenyl)-(4-phenyl)indenylzirconium dichloride
dimethylsilanediyl(2-n-propyl-4-(4'-cyclohexylphenyl)
  indenyl)-(4-phenyl)indenylzirconium dichloride
dimethylsilanediyl(2-n-propyl-4-(4'-sec-butylphenyl)
  indenyl)-(4-phenyl)indenylzirconium dichloride
dimethylsilanediyl(2-n-propyl-4-(4'-tert-butylphenyl)
  indenyl)-(4-phenyl)indenylzirconium dichloride
dimethylsilanediyl(2-n-butyl-4-phenyl)indenyl)-(4-
  phenyl)indenyl)zirconium dichloride
dimethylsilanediyl(2-n-butyl-4-(4'-methylphenyl)
  indenyl)-(4-phenyl)indenyl)zirconium dichloride
dimethylsilanediyl(2-n-butyl-4-(4'-ethylphenyl)indenyl)-
  (4-phenyl)indenyl)zirconium dichloride
dimethylsilanediyl(2-n-butyl-4-(4'-n-propylphenyl)
  indenyl)-(4-phenyl)indenylzirconium dichloride
dimethylsilanediyl(2-n-butyl-4-(4'-isopropylphenyl)
  indenyl)-(4-phenyl)indenylzirconium dichloride
dimethylsilanediyl(2-n-butyl-4-(4'-n-butylphenyl)
  indenyl)-(4-phenyl)indenylzirconium dichloride
dimethylsilanediyl(2-n-butyl-4-(4'-hexylphenyl)indenyl)-
  (4-phenyl)indenyl)zirconium dichloride
dimethylsilanediyl(2-n-butyl-4-(4'-cyclohexylphenyl)
  indenyl)-(4-phenyl)indenylzirconium dichloride
dimethylsilanediyl(2-n-butyl-4-(4'-sec-butylphenyl)
  indenyl)-(4-phenyl)indenylzirconium dichloride
dimethylsilanediyl(2-n-butyl-4-(4'-tert-butylphenyl)
  indenyl)-(4-phenyl)indenylzirconium dichloride
dimethylsilanediyl(2-hexyl-4-phenyl)indenyl)-(4-phenyl)
  indenyl)zirconium dichloride
dimethylsilanediyl(2-hexyl-4-(4'-methylphenyl)indenyl)-
  (4-phenyl)indenyl)zirconium dichloride
dimethylsilanediyl(2-hexyl-4-(4'-ethylphenyl)indenyl)-
  (4-phenyl)indenyl)zirconium dichloride
dimethylsilanediyl(2-hexyl-4-(4'-n-propylphenyl)
  indenyl)-(4-phenyl)indenyl)zirconium dichloride
dimethylsilanediyl(2-hexyl-4-(4'-isopropylphenyl)
  indenyl)-(4-phenyl)indenylzirconium dichloride
dimethylsilanediyl(2-hexyl-4-(4'-n-butylphenyl)indenyl)-
  (4-phenyl)indenyl)zirconium dichloride
dimethylsilanediyl(2-hexyl-4-(4'-hexylphenyl)indenyl)-
  (4-phenyl)indenyl)zirconium dichloride
dimethylsilanediyl(2-hexyl-4-(4'-cyclohexylphenyl)
  indenyl)-(4-phenyl)indenylzirconium dichloride
dimethylsilanediyl(2-hexyl-4-(4'-sec-butylphenyl)
  indenyl)-(4-phenyl)indenyl)zirconium dichloride
dimethylsilanediyl(2-hexyl-4-(4'-tert-butylphenyl)
  indenyl)-(4-phenyl)indenylzirconium dichloride
dimethylsilanediyl(2-methylazapentalene)(4-phenyl)
  indenylzirconium dichloride
dimethylsilanediyl(2-methyl-thiapentalene) (4-phenyl)
  indenylzirconium dichloride
dimethylsilanediyl(2-methylphosphapentalene)(4-
  phenyl)indenylzirconium dichloride
dimethylsilanediyl(2-ethylazapentalene)(4-phenyl)
  indenylzirconium dichloride
dimethylsilanediyl(2-ethylthiapentalene)(4-phenyl)
  indenylzirconium dichloride
dimethylsilanediyl(2-ethylphosphapentalene)(4-phenyl)
  indenylzirconium dichloride
dimethylsilanediyl(2-methyl-4-(4'-tert-butylphenyl)
  indenyl)-(4,5-benzo-1-indenyl)zirconium dichloride
dimethylsilanediyl(2-methyl-4-(4'-tert-butylphenyl)
  indenyl)-(4,5-benzo-1-indenyl)hafnium dichloride
dimethylsilanediyl(2-methyl-4-(4'-tert-butylphenyl)
  indenyl)-(4,5-benzo-1-indenyl)titanium dichloride
dimethylsilanediyl(2-methyl-4-(4'-methylphenyl)
  indenyl)-(4,5-benzo-1-indenyl)zirconium dichloride
dimethylsilanediyl(2-methyl-4-(4'-ethylphenyl)indenyl)-
  (4,5-benzo-1-indenyl)zirconium dichloride
dimethylsilanediyl(2-methyl-4-(4'-n-propylphenyl)
  indenyl)-(4,5-benzo-1-indenyl)zirconium dichloride
dimethylsilanediyl(2-methyl-4-(4'-isopropylphenyl)
  indenyl)-(4,5-benzo-1-indenyl)zirconium dichloride
dimethylsilanediyl(2-methyl-4-(4'-n-butylphenyl)
  indenyl)-(4,5-benzo-1-indenyl)zirconium dichloride
dimethylsilanediyl(2-methyl-4-(4'-hexylphenyl)indenyl)-
  (4,5-benzo-1-indenyl)zirconium dichloride
dimethylsilanediyl(2-methyl-4-(4'-sec-butylphenyl)
  indenyl)-(4,5-benzo-1-indenyl)zirconium dichloride
dimethylsilanediyl(9-fluorenyl)-(4,5-benzo-1-indenyl)
  zirconium dichloride
dimethylsilanediyl(9-(2,7-di-tert-butyl)fluorenyl)-(4,5-
  benzo-1-indenyl)zirconium dichloride
dimethylsilanediyl(4-naphthylindenyl)(2-methyl-4-(4'-
  tert-butylphenyl)indenyl)zirconium dichloride
dimethylsilanediyl(2-methylbenzoindenyl)-(4,5-benzo-1-
  indenyl)zirconium dichloride
dimethylsilanediyl(2-methylindenyl)(4,5-benzo-1-
  indenyl)zirconium dichloride
dimethylsilanediyl(2-methyl-4-(1-naphthyl)indenyl)-(4,
  5-benzo-1-indenyl)zirconium dichloride
dimethylsilanediyl(2-methyl-4-(2-naphthyl)(4,5-benzo-
  1-indenyl)zirconium dichloride
dimethylsilanediyl(2-methyl-4-t-butylindenyl)-(4,5-
  benzo-1-indenyl)zirconium dichloride
dimethylsilanediyl(2-methyl-4-ethylindenyl)-(4,5-benzo-
  1-indenyl)zirconium dichloride dimethylsilanediyl(2-methyl-4-acenaphthindenyl)-(4,5-benzo-1-indenyl)zirconium dichloride
dimethylsilanediyl(2-ethylindenyl) (4,5-benzo-1-indenyl)zirconium dichloride
dimethylsilanediyl(2-ethyl-4-ethylindenyl)-(4,5-benzo-1-indenyl)zirconium dichloride
dimethylsilanediyl(2-ethyl-4-phenylindenyl)-(4,5-benzo-1-indenyl)zirconium dichloride
dimethylsilanediyl(2-methyl-4-(tert-butylphenylindenyl)-(4,5-benzo-1-indenyl)zirconium dichloride
dimethylsilanediyl(2-methyl-4-(4-methylphenylindenyl)-(4,5-benzo-1-indenyl)zirconium dichloride
dimethylsilanediyl(2-methyl-4-(4-ethyl-phenylindenyl)-(4,5-benzo-1-indenyl)zirconium dichloride
dimethylsilanediyl(2-methyl-4-(4-trifluoromethylphenylindenyl)-(4,5-benzo-1-indenyl)zirconium dichloride
dimethylsilanediyl(2-methyl-4-(4-methoxyphenylindenyl)-(4,5-benzo-1-indenyl)zirconium dichloride
dimethylsilanediyl(2-ethyl-4-(4-tert-butylphenylindenyl)-(4,5-benzo-1-indenyl)zirconium dichloride
dimethylsilanediyl(2-ethyl-4-(4-methylphenylindenyl)-(4,5-benzo-1-indenyl)zirconium dichloride
dimethylsilanediyl(2-ethyl-4-(4-ethylphenylindenyl)-(4,5-benzo-1-indenyl)zirconium dichloride
dimethylsilanediyl(2-ethyl-4-(4-trifluoromethylphenylindenyl)-(4,5-benzo-1-indenyl)zirconium dichloride
dimethylsilanediyl(2-ethyl-4-(4-methoxyphenylindenyl)-(4,5-benzo-1-indenyl)zirconium dichloride
dimethylsilanediyl(2-methyl-4-(4'-hexylphenyl)indenyl)-(4,5-benzo-1-indenyl)zirconium dichloride
dimethylsilanediyl(2-methyl-4-(4'-sec-butylphenyl)indenyl)-(4,5-benzo-1-indenyl)zirconium dichloride
dimethylsilanediyl(2-ethyl-4-phenyl)indenyl)-(4,5-benzo-1-indenyl)zirconium dichloride
dimethylsilanediyl(2-ethyl-4-(4'-methylphenyl)indenyl)-(4,5-benzo-1-indenyl)zirconium dichloride
dimethylsilanediyl(2-ethyl-4-(4'-ethylphenyl)indenyl)-(4,5-benzo-1-indenyl)zirconium dichloride
dimethylsilanediyl(2-ethyl-4-(4'-isopropylphenyl)indenyl)-(4,5-benzo-1-indenyl)zirconium dichloride
dimethylsilanediyl(2-ethyl-4-(4'-n-butylphenyl)indenyl)-(4,5-benzo-1-indenyl)zirconium dichloride
dimethylsilanediyl(2-ethyl-4-(4'-hexylphenyl)indenyl)-(4,5-benzo-1-indenyl)zirconium dichloride
dimethylsilanediyl(2-ethyl-4-(4'-pentylphenyl)indenyl)-(4,5-benzo-1-indenyl)zirconium dichloride
dimethylsilanediyl(2-ethyl-4-(4'-cyclohexylphenyl) indenyl)-(4,5-benzo-1-indenyl)zirconium dichloride
dimethylsilanediyl(2-ethyl-4-(4'-sec-butylphenyl) indenyl)-(4,5-benzo-1-indenyl)zirconium dichloride
dimethylsilanediyl(2-ethyl-4-(4'-tert-butylphenyl) indenyl)-(4,5-benzo-1-indenyl)zirconium dichloride
dimethylsilanediyl(2-n-propyl-4-phenyl)indenyl)-(4,5-benzo-1-indenyl)zirconium dichloride
dimethylsilanediyl(2-n-propyl-4-(4'-methylphenyl) indenyl)-(4,5-benzo-1-indenyl)zirconium dichloride
dimethylsilanediyl(2-n-propyl-4-(4'-ethylphenyl) indenyl)-(4,5-benzo-1-indenyl)zirconium dichloride
dimethylsilanediyl(2-n-propyl-4-(4'-n-propylphenyl) indenyl)-(4,5-benzo-1-indenyl)zirconium dichloride
dimethylsilanediyl(2-n-propyl-4-(4'-isopropylphenyl) indenyl)-(4,5-benzo-1-indenyl)zirconium dichloride
dimethylsilanediyl(2-n-propyl-4-(4'-n-butylphenyl) indenyl)-(4,5-benzo-1-indenyl)zirconium dichloride
dimethylsilanediyl(2-n-propyl-4-(4'-hexylphenyl) indenyl)-(4,5-benzo-1-indenyl)zirconium dichloride
dimethylsilanediyl(2-n-propyl-4-(4'-cyclohexylphenyl) indenyl)-(4,5-benzo-1-indenyl)zirconium dichloride
dimethylsilanediyl(2-n-propyl-4-(4'-sec-butylphenyl) indenyl)-(4,5-benzo-1-indenyl)zirconium dichloride
dimethylsilanediyl(2-n-propyl-4-(4'-tert-butylphenyl) indenyl)-(4,5-benzo-1-indenyl)zirconium dichloride
dimethylsilanediyl(2-n-butyl-4-phenyl)indenyl)-(4,5-benzo-1-indenyl)zirconium dichloride
dimethylsilanediyl(2-n-butyl-4-(4'-methylphenyl) indenyl)-(4,5-benzo-1-indenyl)zirconium dichloride
dimethylsilanediyl(2-n-butyl-4-(4'-ethylphenyl)indenyl)-(4,5-benzo-1-indenyl)zirconium dichloride
dimethylsilanediyl(2-n-butyl-4-(4'-n-propylphenyl) indenyl)-(4,5-benzo-1-indenyl)zirconium dichloride
dimethylsilanediyl(2-n-butyl-4-(4'-isopropylphenyl) indenyl)-(4,5-benzo-1-indenyl)zirconium dichloride
dimethylsilanediyl(2-n-butyl-4-(4'-n-butylphenyl) indenyl)-(4,5-benzo-1-indenyl)zirconium dichloride
dimethylsilanediyl(2-n-butyl-4-(4'-hexylphenyl)indenyl)-(4,5-benzo-1-indenyl)zirconium dichloride
dimethylsilanediyl(2-n-butyl-4-(4'-cyclohexylphenyl) indenyl)-(4,5-benzo-1-indenyl)zirconium dichloride
dimethylsilanediyl(2-n-butyl-4-(4'-sec-butylphenyl) indenyl)-(4,5-benzo-1-indenyl)zirconium dichloride
dimethylsilanediyl(2-n-butyl-4-(4'-tert-butylphenyl) indenyl)-(4,5-benzo-1-indenyl)zirconium dichloride
dimethylsilanediyl(2-hexyl-4-phenyl)indenyl)-(4,5-benzo-1-indenyl)zirconium dichloride
dimethylsilanediyl(2-hexyl-4-(4'-methylphenyl)indenyl)-(4,5-benzo-1-indenyl)zirconium dichloride
dimethylsilanediyl(2-hexyl-4-(4'-ethylphenyl)indenyl)-(4,5-benzo-1-indenyl)zirconium dichloride
dimethylsilanediyl(2-hexyl-4-(4'-n-propylphenyl) indenyl)-(4,5-benzo-1-indenyl)zirconium dichloride
dimethylsilanediyl(2-hexyl-4-(4'-isopropylphenyl) indenyl)-(4,5-benzo-1-indenyl)zirconium dichloride
dimethylsilanediyl(2-hexyl-4-(4'-n-butylphenyl)indenyl)-(4,5-benzo-1-indenyl)zirconium dichloride
dimethylsilanediyl(2-hexyl-4-(4'-hexylphenyl)indenyl)-(4,5-benzo-1-indenyl)zirconium dichloride
dimethylsilanediyl(2-hexyl-4-(4'-cyclohexylphenyl) indenyl)-(4,5-benzo-1-indenyl)zirconium dichloride
dimethylsilanediyl(2-hexyl-4-(4'-sec-butylphenyl) indenyl)-(4,5-benzo-1-indenyl)zirconium dichloride
dimethylsilanediyl(2-hexyl-4-(4'-tert-butylphenyl) indenyl)-(4,5-benzo-1-indenyl)zirconium dichloride
dimethylsilanediyl(2-methylazapentalene)(4,5-benzo-1-indenyl)zirconium dichloride
dimethylsilanediyl(2-methylthiapentalene)(4,5-benzo-1-indenyl)zirconium dichloride
dimethylsilanediyl(2-methylphosphapentalene)-(4,5-benzo-1-indenyl)zirconium dichloride
dimethylsilanediyl(2-ethylazapentalene)(4,5-benzo-1-indenyl)zirconium dichloride.

Preference is also given to the corresponding dimethylzirconium compounds, the corresponding zirconium-$\eta^4$-butadiene compounds and also the Si(MeEt), Si(PhMe), Si(PHEt) and Si(Et)$_2$ bridges.

The novel metallocenes of the formulae I and II are highly active catalyst components for the polymerization of olefins. Depending on the substitution pattern of the ligands, the metallocenes can be obtained as isomer mixtures. The metallocenes are preferably used as pure isomers for the polymerization.

The rac isomeric metallocenes of the formula II are preferably used.

The novel metallocenes of the formulae I and II are suitable, in particular, as constituents of catalyst systems for preparing polyolefins by polymerization of at least one olefin in the presence of a catalyst comprising at least one cocatalyst and at least one metallocene. For the purposes of the present invention, the term polymerization includes both homopolymerization and copolymerization.

The novel metallocenes of the formulae I and II, particularly those of the formula II, can be used for the polymerization of one or more olefins of the formula $R^1$—CH=CH—$R^b$, where $R^a$ and $R^b$ are identical or different and are each a hydrogen atom or a hydrocarbon having from 1 to 20 carbon atoms, in particular from 1 to 10 carbon atoms, and $R^a$ and $R^b$ together with the atoms connecting them may form one or more rings. Examples of such olefins are 1-olefins having 2–40, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. Preference is given to homopolymerizing ethylene or propylene or copolymerizing ethylene with one or more cyclic olefins such as norbornene and/or one or more dienes having from 4 to 20 carbon atoms, e.g. 1,3-butadiene or 1,4-hexadiene. Examples of such copolymers are ethylene-norbornene copolymers, ethylene-propylene copolymers and ethylene-propylene-1,4-hexadiene copolymers. Particular preference is given to the polymerization of propylene to form isotactic polypropylene having a low molar mass of 50,000–300,000, with very particular preference being given to molar masses of 70,000–200,000.

The polymerization is carried out at from −60 to 300° C., preferably from 50 to 200° C., very particularly preferably from 50 to 80° C. The pressure is from 0.5 to 2000 bar, preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used preferably comprises one of the metallocene compounds of the present invention. It is also possible to use mixtures of two or more metallocene compounds, e.g. for preparing polyolefins having a broad or multimodal molar mass distribution.

The cocatalyst component which together with a novel metallocene of the formula I or II forms the catalyst system comprises at least one compound of the aluminoxane type or a Lewis acid or an ionic compound which reacts with a metallocene to convert it into a cationic compound.

As aluminoxane, preference is given to using a compound of the formula (III)

$$(R\,AlO)_n \qquad (III).$$

Further suitable aluminoxanes can be, for example, cyclic as in formula (IV)

or linear as in formula (V)

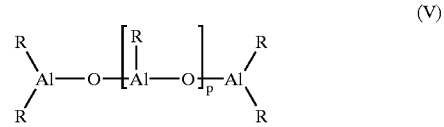

or of the cluster type as in formula (VI)

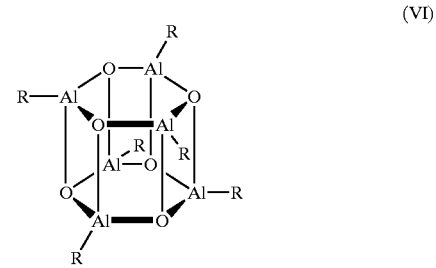

Such aluminoxanes are described, for example, in JACS 117 (1995), 6465–74, organometallics 13 (1994), 2957–2969.

The radicals R in the formulae (III), (IV), (V) and (VI) may be identical or different and are each a $C_1$–$C_{20}$-hydrocarbon group such as a $C_1$–$C_6$-alkyl group, a $C_6$–$C_{16}$-aryl group, benzyl or hydrogen, and p is an integer from 2 to 50, preferably from 10 to 35.

The radicals R are preferably identical and are preferably methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in a proportion of 0.01–40% (of the number of radicals R).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (e.g. toluene).

To prepare an aluminoxane having different alkyl groups R, two different trialkylaluminums (AlR$_3$+AlR'$_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form or as an adduct.

As Lewis acid, preference is given to using at least one organoboron or organoaluminum compound containing $C_1$–$C_{20}$-groups such as branched or unbranched alkyl or haloalkyl, e.g. methyl, propyl, isopropyl, isobutyl or trifluoromethyl, or unsaturated groups such as aryl or haloaryl, e.g. phenyl, tolyl, benzyl, p-fluorophenyl, 3,5-difluorophenyl, pentachlorophenyl, pentafluorophenyl, 3,4,5-trifluorophenyl or 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which contain a noncoordinating anion, for example tetrakis(pentafluorophenyl)borate, tetraphenylborate, $SbF_6^-$, $CF_3SO_3^-$ or $ClO_4^-$. Cationic counterions used are protonated Lewis bases such as methylamine, aniline, N,N-dimethylbenzylamine and derivatives, N,N-dimethylcyclohexylamine and derivatives, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene and triphenylcarbenium.

Examples of such ionic compounds which can be used according to the present invention are triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
N,N-dimethylcyclohexylammonium tetrakis(pentafluorophenyl)borate,
N,N-dimethylbenzylammonium tetrakis(pentafluorophenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Further useful cocatalyst components are borane or carborane compounds such as 7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14),
bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Useful cocatalyst systems are likewise combinations of at least one of the abovementioned amines and a support with organoelement compounds as described in the Patent WO 99/40129.

Preferred constituents of these cocatalyst systems are the compounds of the formulae (A) and (B),

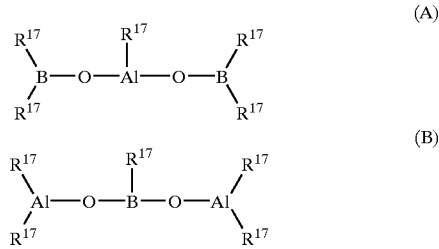

where $R^{17}$ is a hydrogen atom, a halogen atom, a $C_1$–$C_{40}$-group, in particular $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{17}$ may also be an —$OSiR_3$ group, where R are identical or different and are as defined for $R^{17}$.

Further preferred cocatalysts are compounds in general which are formed by reaction of at least one compound of the formula (C) and/or (D) and/or (E) with at least one compound of the formula (F).

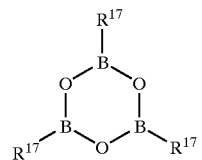

-continued

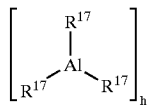
(F)

where

R[7] may be a hydrogen atom or a boron-free $C_1$–$C_{40}$-group such as $C_1$–$C_{20}$-alkyl, $C_6$–$C_{20}$-aryl, $C_7$–$C_{40}$-arylalky or $C_7$–$C_{40}$-alkylaryl, and R[17] is as defined above, X is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl, D is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl, f is an integer from 0 to 3, g is an integer from 0 to 3, where f+g is not equal to 0, h is an integer from 1 to 10.

If desired, the organoelement compounds are combined with an organometallic compound of the formula III to VI and/or VII $[M^4R^{19}_q]_k$, where $M^4$ is an element of main group I, II or III of the Periodic Table of the Elements, $R^{19}$ are identical or different and are each a hydrogen atom, a halogen atom or a $C_1$–$C_{40}$-group, in particular a $C_1$–$C_{20}$-alkyl group, a $C_6$–$C_{40}$-aryl group, a $C_7$–$C_{40}$-arylalkyl group or a $C_7$–$C_{40}$-alkylaryl group, q is an integer from 1 to 3 and k is an integer from 1 to 4.

Examples of cocatalytically active compounds of the formulae A and B are

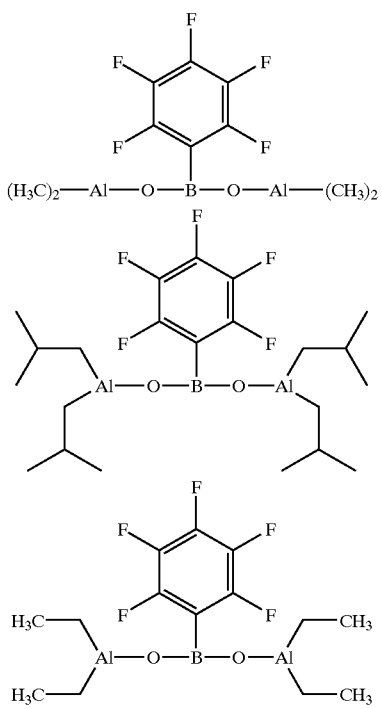

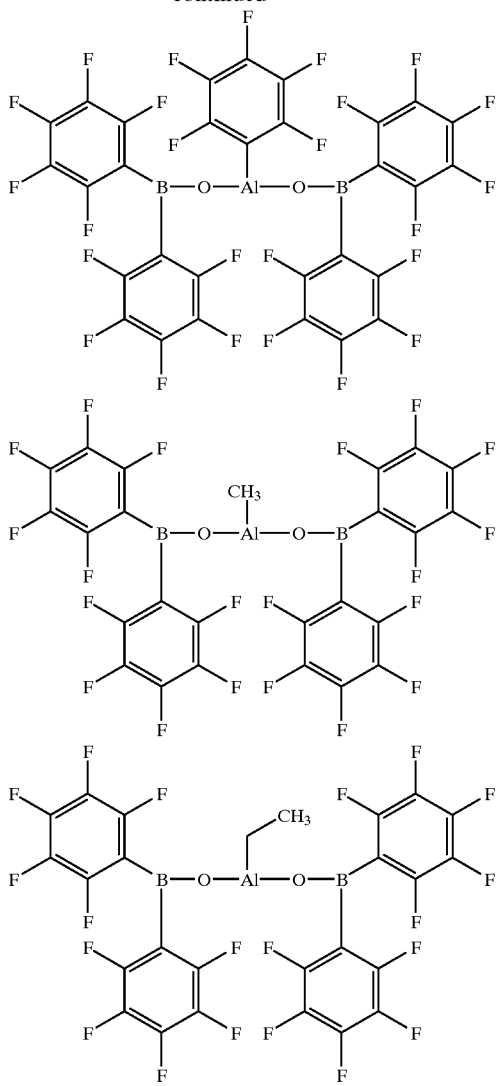

The organometallic compounds of the formula VII are preferably uncharged Lewis acids in which $M^4$ is lithium, magnesium and/or aluminum, in particular aluminum. Examples of the preferred organometallic compounds of the formula VIII are trimethylaluminum, triethylaluminum; triisopropylaluminum, trihexylaluminum, trioctylaluminum, tri-n-butylaluminum, tri-n-propylaluminum, triisoprenaluminum, dimethylaluminum monochloride, diethylaluminum monochloride, diisobutylaluminum monochloride, methylaluminum sesquichloride, ethylaluminum sesquichloride, dimethylaluminum hydride, diethylaluminum hydride, diisopropylaluminum hydride, dimethylaluminum trimethylsiloxide, dimethylaluminum triethylsiloxide, phenylalane, pentafluorphenylalane and o-tolylalane.

Further useful cocatalysts, which may be in unsupported or supported form, are the compounds described in EP-A-924223, DE 19622207.9, EP-A-601830, EP-A-824112, EP-A-824113, EP-A-811627, WO97/11775 and DE 19606167.9.

The support component of the catalyst system of the present invention can be any organic or inorganic, inert solid, in particular a porous support such as talc, inorganic oxides and finely divided polymer powders (e.g. polyolefins).

Suitable inorganic oxides may be found among those of groups 2, 3, 4, 5, 13, 14, 15 and 16 of the Periodic Table of the Elements. Examples of oxides preferred as supports include silicon dioxide, aluminum oxide and mixed oxides of the two elements and corresponding oxide mixtures. Other inorganic oxides which can be used either alone or in combination with the last-named preferred oxidic supports are, for example, MgO, $ZrO_2$, $TiO_2$ or $B_2O_3$, to name only a few.

The support materials used have a specific surface area in the range from 10 to 1000 $m^2/g$, a pore volume in the range from 0.1 to 5 ml/g and a mean particle size of from 1 to 500 $\mu m$. Preference is given to supports having a specific surface area in the range from 50 to 500 $m^2/g$, a pore volume in the range from 0.5 to 3.5 ml/g and a mean particle size in the range from 5 to 350 $\mu m$. Particular preference is given to supports having a specific surface area in the range from 200 to 400 $m^2/g$, a pore volume in the range from 0.8 to 3.0 ml/g and a mean particle size of from 10 to 200 $\mu m$.

If the support material used naturally has a low moisture content or residual solvent content, dehydration or drying before use can be omitted. If this is not the case, for example when using silica gel as support material, dehydration or drying is advisable. Thermal dehydration or drying of the support material can be carried out under reduced pressure and simultaneous blanketing with inert gas (e.g. nitrogen). The drying temperature is in the range from 100 to 1000° C., preferably from 200 to 800° C. In this case, the pressure is not critical. The duration of the drying process can be from 1 to 24 hours. Shorter or longer drying times are possible, provided that equilibrium with the hydroxyl groups on the support surface can be established under the conditions selected, which normally takes from 4 to 8 hours.

Dehydration or drying of the support material can also be carried out by chemical means, by reacting the adsorbed water and the hydroxyl groups on the surface with suitable passivating agents. The reaction with the passivating reagent enables the hydroxyl groups to be converted completely or partly into a form which leads to no adverse interaction with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting, in the absence of air and moisture, a suspension of the support material in a suitable solvent with the passivating reagent in pure form or as a solution in a suitable solvent. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are also possible. The reaction time is from 30 minutes to 20 hours, preferably from 1 to 5 hours. After the chemical dehydration is complete, the support material is isolated by filtration under inert conditions, washed one or more times with suitable inert solvents as described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities before use by means of appropriate purification and drying operations.

According to the present invention, the catalyst system is produced by mixing at least one metallocene as rac/meso isomer mixture, at least one cocatalyst and at least one passivated support.

To prepare the supported catalyst system, at least one of the above-described metallocene components is brought into contact in a suitable solvent with at least one cocatalyst component, preferably giving a soluble reaction product, an adduct or a mixture. The preparation obtained in this way is then mixed with the dehydrated or passivated support material, the solvent is removed and the resulting supported metallocene catalyst system is dried to ensure that the solvent is completely or mostly removed from the pores of the support material. The supported catalyst is obtained as a free-flowing powder.

A process for producing a free-flowing and, if desired, prepolymerized supported catalyst system comprises the following steps:

a) preparation of a metallocene/cocatalyst mixture in a suitable solvent or suspension medium, where the metallocene component has one of the above-described structures;

b) application of the metallocene/cocatalyst mixture to a porous, preferably inorganic dehydrated support;

c) removal of the major part of the solvent from the resulting mixture;

d) isolation of the supported catalyst system;

e) if desired, prepolymerization of the supported catalyst system obtained using one or more olefinic monomer(s) so as to obtain a prepolymerized supported catalyst system.

Preferred solvents for preparing the metallocene/cocatalyst mixture are hydrocarbons and hydrocarbon mixtures which are liquid at the reaction temperature selected and in which the individual components preferably dissolve. However, solubility of the individual components is not a prerequisite as long as it is ensured that the reaction product of metallocene and cocatalyst components is soluble in the solvent chosen. Examples of suitable solvents encompass alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and metallocene used for producing the supported catalyst system can be varied within a wide range. Preference is given to using a molar ratio of aluminum to the transition metal in the metallocene of from 10:1 to 1000:1, very particularly preferably from 50:1 to 500:1.

In the case of methylaluminoxane, preference is given to using 30% strength solutions in toluene; however, the use of 10% strength solutions is also possible.

To preactivate the metallocene, the solid metallocene is dissolved in a solution of the aluminoxane in a suitable solvent. It is also possible to dissolve the metallocene separately in a suitable solvent and subsequently to combine this solution with the aluminoxane solution. Preference is given to using toluene.

The preactivation time is from 1 minute to 200 hours. The preactivation can take place at room temperature (25° C.). The use of higher temperatures can, in particular cases, shorten the preactivation time required and effect an additional increase in the activity. In this case, higher temperatures means a range from 50 to 100° C.

The preactivated solution or the metallocene/cocatalyst mixture is subsequently combined with an inert support material, usually silica gel, in the form of a dry powder or as a suspension in one of the abovementioned solvents. The support material is preferably used as a powder. The order of addition is unimportant. The preactivated metallocene/cocatalyst solution or the metallocene/cocatalyst mixture can be added to the support material or else the support material can be introduced into the solution.

The volume of the preactivated solution or metallocene/cocatalyst mixture can exceed 100% of the total pore volume of the support material used or else be up to 100% of the total pore volume.

The temperature at which the preactivated solution or metallocene/cocatalyst mixture is brought into contact with the support material can vary within a range from 0 to 100° C., although higher or lower temperatures are also possible.

Subsequently, all or most of the solvent is removed from the supported catalyst system, with the mixture being able to be stirred and, if desired, heated. Preference is given to removing both the visible proportion of solvent and also that present in the pores of the support material. Removal of the solvent can be carried out in a conventional manner using reduced pressure and/or purging with inert gas. In the drying process, the mixture can be heated until the free solvent has been removed, which usually takes from 1 to 3 hours at a temperature of preferably from 30 to 60° C. The free solvent is the visible proportion of solvent in the mixture, and residual solvent is the proportion which is enclosed in the pores. As an alternative to complete removal of solvent, it is also possible to dry the supported catalyst system only to a certain residual solvent content, with the free solvent having been completely removed. The supported catalyst system can subsequently be washed with a low-boiling hydrocarbon such as pentane or hexane and dried again.

The supported catalyst system obtained can either be used directly for the polymerization of olefins or be prepolymerized using one or more olefinic monomers prior to its use in a polymerization process. The prepolymerization of supported catalyst systems is described, for example, in WO 94/28034.

As additive, it is possible to add a small amount of an olefin, preferably an a-olefin (for example styrene or phenyldimethylvinylsilane) as activity-increasing component or, for example, an antistatic during or after production of the supported catalyst system.

As antistatic, it is usual to use a mixture of a metal salt of Medialan acid, a metal salt of anthranilic acid and a polyamine. Such antistatics are described, for example, in EP-A-0,636,636.

The molar ratio of additive to metallocene component compound (I)is preferably from 1:1000 to 1000:1, very particularly preferably from 1:20 to 20:1.

The present invention also provides a process for preparing a polyolefin having a low molar mass of 50,000–300,000, with molar masses of 70,000–250,000 being very particularly preferred, by polymerization of one or more olefins in the presence of a catalyst system comprising at least one transition metal component in the form of the novel metallocenes of the formula I or II. For the purposes of the present invention, the term polymerization covers both homopolymerization and copolymerization. In order to produce saturated chain ends and thus achieve a fine adjustment of the molar masses (of the MFI), it is possible, if desired, to meter in a small amount of hydrogen during the polymerization.

The catalyst system described can be used as sole catalyst component for the polymerization of olefins having from 2 to 20 carbon atoms, but is preferably used in combination with at least one alkyl compound of the elements of main groups I to III of the Periodic Table, e.g. an aluminum alkyl, magnesium alkyl or lithium alkyl or an aluminoxane. The alkyl compound is added to the monomer or suspension medium and serves to free the monomer of substances which can adversely affect the catalyst activity. The amount of alkyl compound added depends on the quality of the monomers used.

In the polymerization, the antistatic can be metered into the polymerization system either together with or separately from the catalyst system used.

The polymers prepared using the catalyst system comprising at least one of the metallocenes of the present invention display a uniform particle morphology and contain no fines. In the polymerization using the catalyst system, no deposits or caking are observed.

The catalyst system gives polymers such as polypropylene which have an extraordinarily high stereospecificity and regiospecificity.

The invention is illustrated by the following examples which do not, however, restrict the scope of the invention.

General procedures: Preparation and handling of organometallic compounds was carried out with exclusion of air and moisture under argon (Schlenk technique or glove box). All solvents required were purged with argon and dried over molecular sieves before use.

The preparation of 7-chloro-1H-indene is carried out by a modified method based on that of D. A. Netzel et al., J. Org. Chem. 1998, 22, 4226–4237. Heteropentalene systems are prepared by a method described by Ewen et al., Metalorganic Catalysts for Synthesis and Polymerisation, 1999, Springer-Verlag, 150–159.

EXAMPLE 1

Preparation of 1-(2-carboxyethyl)-2-chlorobenzene

A solution of 171.0 g (2.51 mol) of sodium ethoxide in ethanol is admixed with 149.2 g (932 mmol) of diethyl malonate. 50.0 g (311 mmol) of 2-chlorobenzyl chloride are added to this reaction mixture, and after the addition is complete the reaction mixture is refluxed for three hours. After cooling to room temperature, 480 g (1.71 mol) of a KOH solution are added and the mixture is subsequently refluxed for another hour. The ethanol is then distilled off and the residue is subjected to an aqueous work-up and extracted three times with 100 ml each time of diethyl ether. The organic phase is discarded and the aqueous phase is brought to a pH of 1 using concentrated HCl. The mixture is subsequently extracted three times with 100 ml each time of diethyl ether. The combined organic phases are washed with 100 ml of water and then with 100 ml of a saturated NaCl solution.

After drying over magnesium sulfate, the solvent is removed in an oil pump vacuum. The residue is taken up in heptane and subsequently heated to 180° C. After gas evolution has ceased, the solvent is removed in an oil pump vacuum. 43.8 g (91%) of the desired product are isolated. The product prepared is used without further purification for the next step.

EXAMPLE 2

Preparation of 4-chloroindanone 33.5 g (181 mmol) of the 1-(2-carboxyethyl)-2-chlorobenzene and 83.4 ml of thionyl chloride are placed in a reaction vessel and stirred at 80° C. for one hour. The excess thionyl chloride is subsequently taken off and the residue is admixed with 200 ml of heptane. The reaction mixture is stirred for 30 minutes and the solvent is subsequently removed in an oil pump vacuum. The residue is taken up in 536 ml of methylene chloride and, while cooling in ice, 48.4 g (363 mmol) of aluminum trichloride are added a little at a time over a period of 10 minutes. The resulting reaction solution is stirred at 0° C. for another 2 hours before the reaction mixture is poured onto 300 ml of ice water. After the aqueous phase has been separated off and extracted once with 60 ml of toluene, the combined organic phases are washed with 80 ml of water and with 100 ml of saturated NaCl solution. After drying over magnesium sulfate, the solvent is removed in an oil pump vacuum. 29 g (96%) of the desired product are isolated.

EXAMPLE 3

Preparation of 4-(4'-tert-butylphenyl)indanone 14.0 g (84 mmol) of 4-chloroindanone, 32.9 g (185 mmol) of 4-tert-butylphenylboronic acid, 230 ml of ethylene glycol and 38 ml of water together with 19.6 g of sodium carbonate are placed in a reaction vessel and degassed three times. A solution of 94 mg (0.42 mmol) of Pd(OAc)$_2$ and 2.1 ml (1.26 mmol) of TPPTS in 2 ml of water is subsequently added. The resulting reaction mixture is refluxed for 5 hours. After cooling, it is extracted three times with toluene and the combined organic phases are washed with saturated NaCl solution. After drying over magnesium sulfate, the solvent is removed in an oil pump vacuum. 21.3 g (96%) of the desired product are isolated.

EXAMPLE 4

Preparation of 4-(4'-tert-butylphenyl)indene 9.0 g (34 mmol) of 4-(4'-tert-butylphenyl)indanone and 1.3 g (34 mmol) of sodium borohydride together with 32 ml of toluene are placed in a reaction vessel. The reaction mixture is heated to 50° C., after which 6.2 ml (148 mmol) of methanol are added over a period of 10 minutes. After the addition is complete, the mixture is stirred at 50° C. for 2 hours. After addition of 30 ml of a saturated ammonium chloride solution, the mixture is stirred for another 30 minutes. After separating off the aqueous phase, the organic phase is washed once with a saturated ammonium chloride solution and once with a saturated sodium chloride solution. After drying over magnesium sulfate, the solvent mixture is removed on a rotary evaporator, the residue is made up to a total volume of 150 ml with toluene and is admixed with 0.2 g of p-toluenesulfonic acid. After 30 minutes, no more elimination of water is observed. The reaction mixture is subsequently washed once with a saturated sodium hydrogen carbonate solution, then dried over magnesium sulfate and the solvent is removed in an oil pump vacuum. 7.3 g (86%) of the desired product are isolated.

4-Phenylidene and 4,5-benzoindene are prepared in a manner analogous to the above synthesis examples.

EXAMPLE 5

Preparation of 2-methyl-4-(4'-tert-butylphenyl)-1-dimethylchlorosilylindene 20.0 g (76 mmol) of 2-methyl-4-(4'-tert-butylphenyl)indene together with 160 ml of toluene and 5 ml of DME are placed in a reaction vessel. 28.4 ml (76 mmol) of a butyllithium solution are added dropwise to the above solution, and after the addition is complete the mixture is stirred at 80° C. for another 1 hour. The resulting reaction solution is slowly added dropwise to a precooled (−40° C.) solution of 27.7 ml (229 mmol) of dimethyldichlorosilane in 260 ml of THF. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent is removed from the filtrate in an oil pump vacuum. 24.8 g (98%) of the desired product are isolated.

$^1$H-NMR (400 MHz, CDCl$_3$): 7.3–7.0 (m, 7H, arom-H), 6.7 (s, 1H, olefin-H-indene), 3.5 (s, 1H, H-indene), 2.1 (s, 3H, CH$_3$), 1.3 (s, 9H, tert-butyl), 0.3, 0.05 (each s, each 3H, CH$_3$—Si).

EXAMPLE 6

Preparation of 2-ethyl-4-(4'-tert-butylphenyl)-1-dimethylchlorosilylindene 20.0 g (72.4 mmol) of 2-ethyl-4-(4'-tert-butylphenyl)indene together with 153 ml of toluene and 4.8 ml of DME are placed in a reaction vessel. 27.0 ml (72.4 mmol) of a butyllithium solution are added dropwise to the above solution, and after the addition is complete the mixture is stirred at 80° C. for another 1 hour. The resulting reaction solution is slowly added dropwise to a precooled (−40° C.) solution of 26.3 ml (217 mmol) of dimethyldichlorosilane in 248 ml of THF. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent is removed from the filtrate in an oil pump vacuum. 25.5 g (95%) of the desired product are isolated.

$^1$H-NMR (400 MHz, CDCl$_3$): 7.3–7.0 (m, 7H, arom-H), 6.7 (s, 1H, olefin-H-indene), 3.6 (s, 1H, H-indene), 2.6, 2.4 (each m, 1H, CH$_2$), 1.3 (s, 9H, tert-butyl), 1.1 (t, 3H, CH$_3$), ( 0.3, 0.0 (each s, each 3H, CH$_3$—Si).

EXAMPLE 7

Preparation of 2-methyl-(4-thiapentalene)-1-dimethylchlorosilane 20.0 g (148 mmol) of 2-methyl-(2-hydrocyclopenta[2,1-b]thiophene) together with 260 ml of toluene and 8 ml of DME are placed in a reaction vessel. 55.3 ml (148 mmol) of a butyllithium solution are added dropwise to the above solution, and after the addition is complete the mixture is stirred at 80° C. for another 1 hour. The resulting reaction solution is slowly added dropwise to a precooled (−40° C.) solution of 53.9 ml (446 mmol) of dimethyldichlorosilane in 460 ml of THF. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent is removed from the filtrate in an oil pump vacuum. 29.1 g (86%) of the desired product are isolated.

$^1$H-NMR (400 MHz, CD$_2$Cl$_2$): 7.3–6.8 (m, 2H), 6.7–6.4 (m, 1H), 4.0–3.4 (m, 2H), 2.6 (m, 3H, CH$_3$), 0.3, −0.05 (each s, each 3H,CH$_3$—Si).

Other indenyldimethylchlorosilane and heteropentalene-dimethylchlorosilane systems can be synthesized in a manner analogous to the above-described examples.

EXAMPLE 8

Preparation of dimethylsilanediyl(2-methyl-4-(4'-tert-butylphenyl)indene)(1-indene)

4.1 g (35.2 mmol) of indene together with 80 ml of toluene and 3 ml of THF are placed in a reaction vessel and admixed with 13.1 ml (35.2 mmol) of butyllithium solution. After the addition is complete, the reaction solution is heated to 80° C. and stirred at this temperature for 1 hour. This solution is subsequently allowed to cool to room temperature and added dropwise at room temperature to a solution of 12.5 g (35.2 mmol) of 2-methyl-4-(4'-tert-butylphenyl)-1-dimethylchlorosilylindene in 150 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 15.0 g (98%) of the desired ligand system are isolated.

$^1$H-NMR (400 MHz, CDCl$_3$): 7.6–7.2 (m, 11H, arom-H), 6.9–7.05 (m, 1H, olefin-H-indene), 6.7, 6.5 (each d, each 1H, H-indene), 3.7, 3.8 (each d, each 1H, indene-H-bridge), 2.35 (d, 3H, CH$_3$), 1.5 (s, 9H, tert-butyl), 0.0, 0.3 (each d, each 3H, Si—CH$_3$).

EXAMPLE 9

Preparation of dimethylsilanediyl(2-ethyl-4-(4'-tert-butylphenyl)indene)(1-indene)

3.9 g (33.9 mmol) of indene together with 77 ml of toluene and 2.9 ml of THF are placed in a reaction vessel and admixed with 12.6 ml (33.9 mmol) of butyllithium solution. After the addition is complete, the reaction solution is heated to 80° C. and stirred at this temperature for 1 hour. This solution is subsequently allowed to cool to room temperature and added dropwise at room temperature to a solution of 12.5 g (33.9 mmol) of 2-ethyl-4-(4'-tert-butylphenyl)-1-dimethylchlorosilylindene in 144 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 14.6 g (96%) of the desired ligand system are isolated.

$^1$H-NMR (400 MHz, CDCl$_3$): 7.6–7.3 (m, 11H, arom-H), 6.95 (d, 1H, olefin-H-indene), 6.7, 6.5 (each d, each 1H, H-indene), 3.8–3.9 (dd, 2H, indene-H-bridge), 2.8,2.6 (each m, each 1H, CH$_2$), 1.5 (s, 9H, tert-butyl), 1.3 (t, 3H, CH$_3$), 0.0, −0.3 (each d, each 3H, Si—CH$_3$).

EXAMPLE 10

Preparation of dimethylsilanediyl(2-methyl-4-(4'-tert-butylphenyl)indene)(4-(4'-tert-butylphenyl)indene)

9.1 g (36.6 mmol) of 4-(4'-tert-butylphenyl)indene together with 83 ml of toluene and 3.1 ml of THF are placed in a reaction vessel and admixed with 13.7 ml (36.6 mmol) of butyllithium solution. After the addition is complete, the reaction solution is heated to 80° C. and stirred at this temperature for 1 hour. This solution is subsequently allowed to cool to room temperature and added dropwise at room temperature to a solution of 13.0 g (36.6 mmol) of 2-methyl-4-(4'-tert-butylphenyl)-1-dimethylchlorosilylindene in 156 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 18.9 g (91%) of the desired ligand system are isolated.

$^1$H-NMR (400 MHz, CDCl$_3$): 7.4–7.0 (m, 14H, arom-H), 6.75 (d, 1H, olefin-H-indene), 6.6, 6.4 (each d, each 1H, H-indene), 3.6–3.5 (dd, 2H, indene-H-bridge), 2.2 (d, 3H, CH$_3$), 1.5, 1.4 (each s, each 9H, tert-butyl), −0.1, −0.3 (each d, each 3H, Si—CH$_3$).

EXAMPLE 11

Preparation of dimethylsilanediyl(2-ethyl-4-(4'-tert-butylphenyl)indene)(4-(4'-tert-butylphenyl)indene)

8.4 g (33.9 mmol) of 4-(4'-tert-butylphenyl)indene together with 77 ml of toluene and 2.9 ml of THF are placed in a reaction vessel and admixed with 12.6 ml (33.9 mmol) of butyllithium solution. After the addition is complete, the reaction solution is heated to 80° C. and stirred at this temperature for 1 hour. This solution is subsequently allowed to cool to room temperature and added dropwise at room temperature to a solution of 12.5 g (33.9 mmol) of 2-ethyl-4-(4'-tert-butylphenyl)-1-dimethylchlorosilylindene in 144 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 17.5 g (89%) of the desired ligand system are isolated.

$^1$H-NMR (400 MHz, CDCl$_3$): 7.4–7.1 (m, 14H, arom-H), 6.85 (d, 1H, olefin-H-indene), 6.6, 6.4 (each d, each 1H, H-indene), 3.7–3.6 (dd, 2H, indene-H-bridge), 2.7, 2.6 (each m, each 1H, CH$_2$), 1.4, 1.3 (each s, each 9H, tert-butyl), 1.2 (t, 3H, CH$_3$), −0.1, −0.3 (each d, each 3H, Si-CH$_3$).

EXAMPLE 12

Preparation of dimethylsilanediyl(2-methyl(thiapentalene)(4-(4'-tert-butylphenyl)indene)

8.4 g (33.9 mmol) of 4-(4'-tert-butylphenyl)indene together with 77 ml of toluene and 2.9 ml of THF are placed in a reaction vessel and admixed with 12.6 ml (33.9 mmol) of butyllithium solution. After the addition is complete, the reaction solution is heated to 800C and stirred at this temperature for 1 hour. This solution is subsequently allowed to cool to room temperature and is added dropwise at room temperature to a solution of 7.7 g (33.9 mmol) of 2-methyl(thiapentalene)-1-dimethylchlorosilane in 140 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 11.3 g (76%) of the desired ligand system are isolated.

$^1$H-NMR (400 MHz, CDCl$_3$): 7.6–6.8 (m, 1OH, arom-H), 6.5 (m, 1H), 6.6, 6.4 (each d, each 1H, H-indene), 3.7–3.6 (dd, 2H), 3.3–3.0 (m, 2H), 2.4 (m, 3H, CH$_3$), 1.45 (s, 9H, tert-butyl-H), −0.1, −0.3 (each d, each 3H,CH$_3$—Si).

EXAMPLE 13

Preparation of dimethylsilanediyl(2-ethyl-4-(4'-tert-butylphenyl)indene)(4-phenylindene)

7.1 g (36.9 mmol) of 4-phenylindene together with 80 ml of toluene and 3.2 ml of THF are placed in a reaction vessel and admixed with 13.7 ml (36.9 mmol) of butyllithium solution. After the addition is complete, the reaction solution is heated to 80° C and stirred at this temperature for 1 hour. This solution is subsequently allowed to cool to room temperature and is added dropwise at room temperature to a solution of 13.6 g (36.9 mmol) of 2-ethyl-4-(4'-tertbutylphenyl)-1-dimethylchlorosilylindene in 150 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 17.0 g (88%) of the desired ligand system are isolated.

$^1$H-NMR (400 MHz, CDCl$_3$): 7.6–7.1 (m, 15H, arom-H), 6.95 (d, 1H, olefin-H-indene), 6.5, 6.3 (each d, each 1H, H-indene), 3.8–3.7 (dd, 2H, indene-H-bridge), 2.7, 2.6 (each m, each 1H, CH$_2$), 1.5 (s, 9H, tert-butyl), 1.1 (t, 3H, CH$_3$), −0.05, −0.3 (each d, each 3H, Si—CH$_3$).

EXAMPLE 14

Preparation of dimethylsilanediyl(2-ethyl-4-(4'-tert-butylphenyl)indene)(4,5-benzoindene)

6.0 g (35.9 mmol) of 4,5-benzoindene together with 80 ml of toluene and 3.2 ml of THF are placed in a reaction vessel and admixed with 13.3 ml (35.9 mmol) of butyllithium solution. After the addition is complete, the reaction solution is heated to 80° C. and stirred at this temperature for 1 hour. This solution is subsequently allowed to cool to room temperature and is added dropwise at room temperature to a solution of 13.2 g (35.9 mmol) of 2-ethyl-4-(4'-tertbutylphenyl)-1-dimethylchlorosilylindene in 150 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum and 15.0 g (84%) of the desired ligand system are isolated.

$^1$H-NMR (400 MHz, CDCl$_3$): 7.6–7.1 (m, 13H, arom-H), 6.8 (d, 1H, olefin-H-indene), 6.7, 6.5 (each d, each 1H, H-indene), 4.0, 3.9 (each d, each 1H, indene-H-bridge), 2.6, 2.4 (each m, each 1H, CH$_2$), 1.4 (s, 9H, tert-butyl), 1.1 (t, 3H, CH$_3$), 0.0, −0.2 (each d, each 3H, Si—CH$_3$).

EXAMPLE 15

Preparation of dimethylsilanediyl(2-methyl-4-(4'-tert-butylphenyl)indenyl)(1-indenyl)zirconium dichloride 6.0 g (13.8 mmol) of dimethylsilanediyl(2-methyl-4-(4'-tert-butylphenyl)indene)(1-indene) and 60 ml of diethyl ether are placed in a reaction vessel and admixed with 10.2 ml (27.6 mmol) of butyllithium solution. After the addition is complete, the reaction solution is stirred overnight at room temperature. It is subsequently cooled to 0° C. and 3.3 g (13.8 mmol) of zirconium tetrachloride are added a little at a time. The resulting suspension is stirred at room temperature for 2 hours. The insoluble lithium chloride is then separated off by means of a G4 frit and washed twice with 40 ml each time of toluene. The solvent is subsequently removed from the filtrate in an oil pump vacuum and the residue which remains is washed with 50 ml of pentane. Drying in an oil pump vacuum gives 6.99 g (85%) of the desired complex.

Pseudo-rac: 7.6–6.9 (m, 13 H, arom-H), 6.2 (d, 1H, H-indene), 2.3 (s, 3H, CH$_3$), 1.4 (s, 9H, tert-butyl), 1.3, 1.1 (each s, each 3H, Si—CH$_3$). Pseudo-meso: 7.7–6.7 (m, 17 H, arom-H), 6.15 (d, 1H, H-indene), 2.4 (s, 3H, CH$_3$), 1.35 (s, 9H, tert-butyl), 1.5 (s, 6H, Si—CH$_3$).

EXAMPLE 16

Preparation of dimethylsilanediyl(2-ethyl-4-(4'-tert-butylphenyl)indenyl)(1-indenyl)zirconium dichloride 5.6 g (12.4 mmol) of dimethylsilanediyl(2-ethyl-4-(4'-tert-butylphenyl)indene)(1-indene) and 70 ml of diethyl ether are placed in a reaction vessel and admixed with 9.4 ml (25.0 mmol) of butyllithium solution. After the addition is complete, the reaction solution is stirred overnight at room temperature. It is subsequently cooled to 0° C. and 2.9 g (12.4 mmol) of zirconium tetrachloride are added a little at a time. The resulting suspension is stirred at room temperature for 2 hours. The insoluble lithium chloride is then separated off by means of a G4 frit and washed twice with 30 ml each time of toluene. The solvent is subsequently removed from the filtrate in an oil pump vacuum and the residue which remains is washed with 50 ml of pentane. Drying in an oil pump vacuum gives 4.7 g (62%) of the desired complex.

Pseudo-rac: 7.6–6.8 (m, 13 H, arom-H), 6.2 (d, 1H, H-indene), 2.6, 2.5 (each m, each 1H, CH$_2$), 1.3 (9H, tert-butyl), 1.4, 1.1 (each s, each 3H, Si—CH$_3$). Pseudo-meso: 7.7–6.7 (m, 17 H, arom-H), 6.15 (d, 1H, H-indene), 2.6 (m, 2H, CH$_2$), 1.35 (s, 9H, tert-butyl), 1.25 (s, 6H, Si—CH$_3$).

EXAMPLE 17

Preparation of dimethylsilanediyl(2-methyl-4-(4'-tert-butylphenyl)indenyl)(4-(4'- tert-butylphenyl)indenyl)zirconium dichloride 6.2 g (10.9 mmol) of dimethylsilanediyl(2-methyl-4-(4'-tert-butylphenyl)indene)(4-(4'-tert-butylphenyl)indene) and 60 ml of diethyl ether are placed in a reaction vessel and admixed with 8.2 ml (21.9 mmol) of butyllithium solution. After the addition is complete, the reaction solution is stirred overnight at room temperature. It is subsequently cooled to 0° C. and 2.6 g (10.9 mmol) of zirconium tetrachloride are added a little at a time. The resulting suspension is stirred at room temperature for 3 hours. The insoluble lithium chloride is then separated off by means of a G3 frit and washed twice with 15 ml each time of THF. The solvent is subsequently removed from the filtrate in an oil pump vacuum. 5.7 g (72%) of the desired complex are isolated.

$^1$H-NMR (400 MHz, CDCl$_3$): Pseudo-rac: 7.6–6.7 (m, 16 H, arom-H), 5.9 (d, 1H, H-indene), 2.1 (s, 3H, CH$_3$), 1.25, 1.2 (each s, each 9H, tert-butyl), 1.4, 1.1 (each s, each 3H, Si—CH$_3$).

Pseudo-meso: 7.6–6.7 (m, 16 H, arom-H), 6.0 (d, 1H, H-indene), 2.2 (s, 3H, CH$_3$), 1.3, 1.15 (each s, each 9H, tert-butyl), 1.5 (s, 6H, Si—CH$_3$).

EXAMPLE 18

Preparation of dimethylsilanediyl(2-ethyl-4-(4'-tert-butylphenyl)indenyl)(4-(4'-tert-butylphenyl)indenyl)zirconium dichloride 18.4 g (31.7 mmol) of dimethylsilanediyl(2-ethyl-4-(4'-tert-butylphenyl)indene)(4-(4'-tert-butylphenyl)indene) and 180 ml of diethyl ether are placed in a reaction vessel and admixed with 23.6 ml (63.3 mmol) of butyllithium solution. After the addition is complete, the reaction solution is stirred overnight at room temperature. It is subsequently cooled to 0° C. and 7.4 g (31.7 mmol) of zirconium tetrachloride are added a little at a time. The resulting suspension is stirred at room temperature for 3 hours. The insoluble lithium chloride is then separated off by means of a G3 frit and washed twice with 40 ml each time of THF. The solvent is subsequently removed from the filtrate in an oil pump vacuum and the residue is stirred with 50 ml of pentane for 1 hour at room temperature. Removal of the pentane and drying of the solid gives 12.9 g (55%) of the desired complex.

$^1$H-NMR (400 MHz, CDCl$_3$): Pseudo-rac: 7.7–6.8 (m, 16 H, arom-H), 6.1 (d, 1H, H-indene), 2.6, 2.5 (each m, each 1H, CH$_2$), 1.25, 1.2 (each s, each 9H, tert-butyl), 1.4, 1.1 (each s, each 3H, Si—CH$_3$). Pseudo-meso: 7.7–6.8 (m, 16 H, arom-H), 6.2 (d, 1H, H-indene), 2.6 (m, 2H, CH$_2$), 1.35, 1.3 (each s, each 9H, tert-butyl), 1.5 (s, 6H, Si—CH$_3$).

EXAMPLE 19

Preparation of dimethylsilanediyl(2-methylthiapentenyl)(4-(4'-tert-butylphenyl)indenyl)zirconium dichloride 11.0 g (25.0 mmol) of dimethylsilanediyl(2-methylthiapentalene)-(4-(4'-tert-butylphenyl)indene) and 160 ml of diethyl ether are laced in a reaction vessel and admixed with 18.7 ml (50.0 mmol) of butyllithium solution. After the addition is complete, the reaction solution is stirred overnight at room temperature. It is subsequently cooled to 0° C. and 5.8 g (25.0 mmol) of zirconium tetrachloride are added a little at a time. The resulting suspension is stirred at room temperature for 2.5 hours. The insoluble lithium chloride is then separated off by means of a G3 frit and washed twice with 30 ml each time of THF. The solvent is subsequently removed from the filtrate in an oil pump vacuum. Drying the solid gives 9.7 g (65%) of the desired complex.

$^1$H-NMR (400 MHz, CDCl$_3$): Pseudo-rac: 7.7–6.8 (m, 11 H, arom-H), 6.6–6.5 (m, 1H, H-thiopentalene), 6.0 (d, 1H, H-indene), 2.1 (m, 3H, CH$_3$), 1.4 (s, 9H, tert-butyl), 1.5, 1.3 (each s, each 3H, Si—CH$_3$). Pseudo-meso: 7.7–6.8 (m, 16 H, arom-H), 6.4–6.2 (m, 1H, H-thiopentalene), 6.1 (d, 1H, H-indene), 2.3 (m, 3H, CH$_3$), 1.3 (s, 9H, tert-butyl), 1.2 (s, 6H, Si—CH$_3$).

EXAMPLE 20

Preparation of dimethylsilanediyl(2-ethyl-4-(4'-tert-butylphenyl)indenyl)(4-phenylindenyl)zirconium dichloride 15.0 g (28.6 mmol) of dimethylsilanediyl(2-ethyl-4-(4'-tertbutylphenyl)indene)(4-phenylindene) and 180 ml of diethyl ether are placed in a reaction vessel and admixed with 21.3 ml (57.2 mmol) of butyllithium solution. After the addition is complete, the reaction solution is stirred at room temperature for 5 hours. It is subsequently cooled to 0° C. and 6.7 g (28.6 mmol) of zirconium tetrachloride are added a little at a time. The resulting suspension is stirred at room temperature for 4 hours. The insoluble lithium chloride is then separated off by means of a G4 frit and washed twice with 40 ml each time of THF. The solvent is subsequently removed from the filtrate in an oil pump vacuum and the residue is stirred with 50 ml of pentane for 1 hour at room temperature. Removal of the pentane and drying the solid gives 8.8 g (45%) of the desired complex.

Pseudo-rac: 7.7–6.7 (m, 17 H, arom-H), 6.0 (d, 1H, H-phenylindene), 2.4, 2.2 (each m, each 1H, CH$_2$), 1.4 (9H, tert-butyl), 1.5, 1.3 (each s, each 3H, Si—CH$_3$). Pseudo-meso: 7.7–6.7 (m, 17 H, arom-H), 6.15 (d, 1H, H-phenylindene), 2.4 (m, 2H, CH$_2$), 1.45 (s, 9H, tert-butyl), 1.1 (s, 6H, Si—CH$_3$).

EXAMPLE 21

Preparation of dimethylsilanediyl(2-ethyl-4-(4'-tert-butylphenyl)indenyl)(4,5- benzoindenyl)zirconium dichloride 15.0 g (30.8 mmol) of dimethylsilanediyl(2-ethyl-4-(4'-tert-butylphenyl)indene)(4,5-benzoindene) and 190 ml of diethyl ether are placed in a reaction vessel and admixed with 21.3 ml (61.6 mmol) of butyllithium solution. After the addition is complete, the reaction solution is stirred at room temperature for 4 hours. It is subsequently cooled to 0° C. and 7.0 g (30.8 mmol) of zirconium tetrachloride are added a little at a time. The resulting suspension is stirred at room temperature for 4 hours. The insoluble lithium chloride is then separated off by means of a G4 frit and washed twice with 40 ml each time of THF. The solvent is subsequently removed from the filtrate in an oil pump vacuum. Recrystallization from THF/pentane gives 7.9 g (40%) of the desired complex.

Pseudo-rac: 8.0–6.9(m, 15 H, arom-H), 6.4 (d, 1H, H-benzoindene), 2.5, 2.3 (each m, each 1H, CH$_2$), 1.4 (9H, tert-butyl), 1.5, 1.3 (each s, each 3H, Si—CH$_3$). Pseudo-meso: 8.0–6.9 (m, 17 H, arom-H), 6.5 (d, 1H, H-benzoindene), 2.5 (m, 2H, CH$_2$), 1.45 (s, 9H, tert-butyl), 1.1 (s, 6H, Si—CH$_3$).

Polymerization

EXAMPLE 22

Heterogeneous polymerization of propene using dimethylsilanediyl-(2-methyl-4-(4'-tert-butylphenyl) indenyl)(1-indenyl)zirconium dichloride Preparation of the catalyst system 53.4 mg (0.09 mmol) of dimethylsilanediyl(2-methyl-4-(4'-tert-butylphenyl)indenyl)(1-indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 5.5 g of a pale pink free-flowing powder.

EXAMPLE 23

Heterogeneous polymerization of propene using dimethylsilanediyl(2-ethyl-4-(4'-tert-butylphenyl) indenyl)(1-indenyl)zirconium dichloride Preparation of the catalyst system 54.8 mg (0.09 mmol) of dimethylsilanediyl(2-ethyl-4-(4'-tert-butylphenyl)indenyl)(1-indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 5.6 g of a pale pink free-flowing powder.

Comparative Example

EXAMPLE 24

Heterogeneous polymerization of propene using dimethylsilanediyl(2-methyl-4-phenylindenyl)-(1-indenyl)zirconium dichloride Preparation of the catalyst system 48.5 mg (0.09 mmol) of dimethylsilanediyl(2-methyl-4-phenylindenyl)(1-indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 5.0 g of a pale pink free-flowing powder.

EXAMPLE 25

Heterogeneous polymerization of propene using (2-methyl-4-(4'-tert-butylphenyl)indenyl)(4-(4'-tert-butylphenyl)indenyl)zirconium dichloride Preparation of the catalyst system 65.4 mg (0.09 mmol) of (2-methyl-4-(4'-tert-butylphenyl)indenyl)-(4-(4'-tert-butylphenyl)indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 6.7 g of a pale pink free-flowing powder.

EXAMPLE 26

Heterogeneous polymerization of propene using (2-ethyl-4-(4'-tert-butylphenyl)indenyl)(4-(4'-tert-butylphenyl)indenyl)zirconium dichloride Preparation of the catalyst system 66.7 mg (0.09 mmol) of (2-ethyl-4-(4'-tert-butylphenyl)indenyl)-(4-(4'-tert-butylphenyl)indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 6.5 g of a pale pink free-flowing powder.

EXAMPLE 27

Heterogeneous polymerization of propene using dimethylsilanediyl(2-methylthiapentenyl)(4-(4'-tert-butylphenyl)indenyl)zirconium dichloride Preparation of the catalyst system 54.0 mg (0.09 mmol) of dimethylsilanediyl(2-methylthiapentenyl)-4-(4'-tert-butylphenyl)indenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 4.9 g of a pale pink free-flowing powder.

EXAMPLE 28

Heterogeneous polymerization of propene using dimethylsilanediyl(2-ethyl-4-(4'-tert-butylphenyl)indenyl)(4-phenylindenyl)zirconium dichloride Preparation of the catalyst system 60.4 mg (0.09 mmol) of dimethylsilanediyl(2-ethyl-4-(4'-tert-butylphenyl)indenyl)(4-phenylindenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 6.1 g of a pale pink free-flowing powder.

EXAMPLE 29

Heterogeneous polymerization of propene using dimethylsilanediyl(2-ethyl-4-(4'-tert-butylphenyl)indenyl)(4,5 benzoindenyl)zirconium dichloride Preparation of the catalyst system 60.3 mg (0.09 mmol) of dimethylsilanediyl(2-ethyl-4-(4'-tert-butylphenyl)indenyl)(4,5-benzoindenyl)zirconium dichloride are dissolved in 4.3 cm$^3$ (20 mmol of Al) of 30% strength methylaluminoxane solution in toluene at room temperature. The solution is diluted with 3.7 cm$^3$ of toluene and stirred at room temperature for 1 hour. This reaction solution is subsequently added a little at a time while stirring to 4 g of SiO$_2$ (MS 948, Grace, dried at 600° C. in a stream of argon) and the mixture is, after addition is complete, stirred for another 10 minutes. The solvent is then removed in an oil pump vacuum until the weight is constant. This gives 6.0 g of a pale pink free-flowing powder.

General description of the polymerization

Polymerization

For introduction into the polymerization system, 1 g of the supported catalyst system is resuspended in 20 cm$^3$ of Exxol.

In parallel thereto, a dry 16 dm$^3$ reactor is flushed first with nitrogen and subsequently with propylene and charged with 10 dm3 of liquid propene. 8 cm$^3$ of a 20% strength trimethylaluminum solution in Varsol are added as scavenger and the mixture is stirred at 30° C. for 15 minutes. The catalyst suspension is subsequently introduced into the reactor. The reaction mixture is heated to the polymerization temperature of 65° C. (4° C./min) and the polymerization system is maintained at 65° C. for 1 hour by cooling. The polymerization is stopped by venting the remaining propylene. The polymer is dried in a vacuum drying oven.

| | Polymerization results | | | | | | | |
|---|---|---|---|---|---|---|---|---|
| Example | 22 | 23 | 24 | 25 | 26 | 27 | 28 | 29 |
| Metallocene (mg)/g of cat. | 9.7 | 9.6 | 9.7 | 9.8 | 10.3 | 11.0 | 9.9 | 10.1 |

-continued

Polymerization results

| Example | 22 | 23 | 24 | 25 | 26 | 27 | 28 | 29 |
|---|---|---|---|---|---|---|---|---|
| PP (g) | 1270* | 1390* | 990* | 1790* | 1990* | 1340* | 1670* | 1560* |
| Activity[1] | 131 | 142 | 102 | 183 | 194 | 121 | 169 | 155 |
| M.p. (iPP) [° C.] | 150 | 151 | 151 | 152 | 154 | 148 | 150 | 151 |
| $M_w/M_n$ | 2.2 | 2.3 | 2.2 | 2.4 | 2.4 | 2.5 | 2.2 | 2.3 |
| $M_w$ | 75,000 | 103,000 | 125,000 | 209,000 | 170,000 | 190,000 | 219,000 | 187,000 |

[1])Activity: kg (polymer)/g of metallocene·h·bar
*no deposit formation in the reactor, free-flowing polymer powder

We claim:

1. A compound of the formula (II)

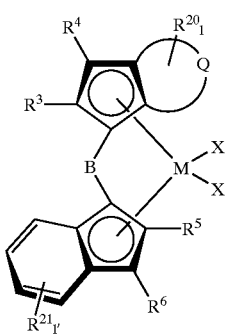

where

M is Ti, Zr or Hf, $R^3$ is a $C_1$–$C_{20}$-group, $R^5$ is a hydrogen atom, $R^4$, $R^6$ are identical or different and are each a hydrogen atom or a $C_1$–$C_{20}$-group, $R^{20}$ $R^{21}$ are identical or different and are each a halogen atom or a $C_1$–$C_{20}$-group, and two radicals $R^{20}$ or $R^{21}$ may form a monocyclic or polycyclic ring system which may in turn be substituted or unsubstituted, X is a halogen atom, Q is a $C_4$–$C_{24}$-aryl ring system which may in turn bear a group $R^{20}$ as substituent or a heteroaryl which together with the cyclopentadienyl ring forms an azapentalene, thiopentalene or phosphapentalene which may in turn bear a group $R^{20}$ as substituent, l, l' are identical or different and are each 1 or 2, B is a bridging structural element between the two cyclopentadienyl moieties.

2. A compound as claimed in claim 1, wherein B is an $M^3R^{13}R^{14}$ group, where $M^3$ is silicon and $R^{13}$ and $R^{14}$ are identical or different and are each a $C_1$–$C_{20}$group.

3. A compound as claimed in claim 2, wherein B is an $Si(Me)_2$, $Si(Ph)_2$, $Si(MeEt)$, $Si(PhMe)$, $Si(PHEt)$, $Si(Et)_2$ group, where Ph is substituted or unsubstituted phenyl, Et is ethyl and Me is methyl.

4. A compound of the formula (IIa)

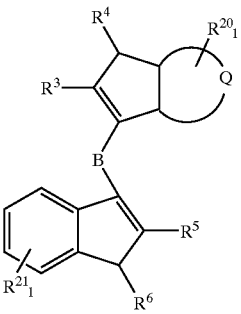

where

M is Ti, Zr or Hf, $R^3$ is a $C_1$–$C_{20}$ group, $R^5$ is a hydrogen atom, $R^4$, $R^6$ are identical or different and are each a hydrogen atom or a $C_1$–$C_{20}$ group, $R^{20}$, $R^{21}$ are identical or different and are each a halogen atom or a $C_1$–$C_{20}$ group, or two radicals $R^{20}$ or $R^{21}$ may form a monocyclic or polycyclic ring system which in turn may be substituted, X is a halogen atom, Q is a $C_4$–$C_{24}$-aryl ring system which may in turn bear a group $R^{20}$ as substituent or a heteroaryl which together with the cyclopentadienyl ring forms an azapentalene, thiopentalene or phosphapentalene which may in turn bear a group $R^{20}$ as substituent, l, l' are identical or different and are each 1 or 2, B is a bridging structural element between the two cyclopentadienyl moieties.

5. The compound of claim 1, wherein

M is Zr, $R^3$ is $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$ is a hydrogen atom, $R^4$, $R^6$ are identical or different and are each a hydrogen atom, $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^{20}$, $R^{21}$ are identical or different and are each a halogen atom, a linear or branched $C_1$–$C_{18}$-alkyl, $C_2$–$C_{10}$- alkenyl, $C_3$–$C_{15}$-alkylalkenyl, a $C_6$–$C_{18}$-aryl group which may be substituted or unsubstituted, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and two radicals $R^{20}$ or $R^{21}$ may form a monocyclic or polycyclic ring system which may in turn be substituted or unsubstituted, X is chlorine, Q is a $C_4$–$C_{24}$-aryl ring system which may in turn bear a group $R^{20}$ as substituent or a heteroaryl which together with the cyclopentadienyl ring forms an azapentalene, thiopentalene or phosphapentalene which may in turn bear a group $R^{20}$ as substituent, l, l' are each 1, B is a bridging structural element between the two cyclopentadienyl moieties.

6. The compound of claim 4

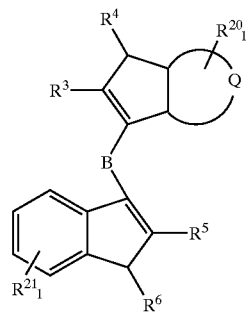

(IIa)

wherein

M is Zr, $R^3$ is a $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$ is a hydrogen atom, $R^4$, $R^6$ are identical or different and are each a hydrogen atom, $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^{20}$, $R^{21}$ are identical or different and are each a halogen atom, a linear or branched $C_1$–$C_{18}$-alkyl, $C_2$–$C_{10}$-alkenyl, $C_3$–$C_{15}$-alkylalkenyl, a $C_6$–$C_{18}$-aryl group which may be substituted, or two radicals $R^{20}$ or $R^{21}$ may form a monocyclic or polycyclic ring system which in turn may be substituted, X is chlorine, Q is a $C_4$–$C_{24}$-aryl ring system which may in turn bear a group $R^{20}$ as substituent or a heteroaryl which together with the cyclopentadienyl ring forms an azapentalene, thiopentalene or phosphapentalene which may in turn bear a group $R^{20}$ as substituent, l, l' are each 1, B is a bridging structural element between the two cyclopentadienyl moieties.

7. The compound of claim 1, wherein B is an $M^3R^{13}R^{14}$ group, where $M^3$ is silicon and $R^{13}$ and $R^{14}$ are identical or different and are each a $C_1$–$C_{20}$ group.

8. The compound of claim 1, wherein B is an $Si(Me)_2$, $Si(Ph)_2$, $Si(MeEt)$, $Si(PhMe)$, $Si(PHEt)$, $Si(Et)_2$ group, where Ph is substituted or unsubstituted phenyl, Et is ethyl and Me is methyl.

9. The compound of claim 7, wherein $R^{13}$ and $R^{14}$ are identical or different and are $C_1$–$C_{10}$-alkyl, $C_6$–$C_{14}$-aryl or trialkylsilyl.

10. The compound of claim 7, wherein $R^{13}$ and $R^{14}$ are identical or different and are trimethylsilyl, triarylsilyl or an alkylarylsilyl group.

11. A compound of the formula (II)

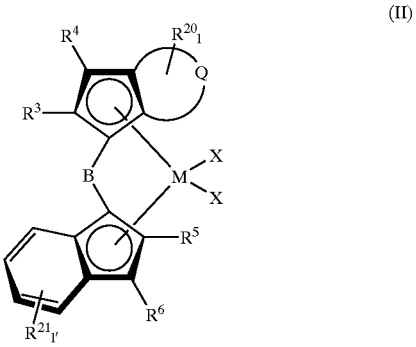

(II)

where

M is Ti, Zr or Hf, $R^3$ is a $C_1$–$C_{20}$-group, $R^5$ is a hydrogen atom, $R^4$, $R^6$ are identical or different and are each a hydrogen atom or a $C_1$–$C_{20}$-group, $R^{20}$, $R^{21}$ are identical or different and are each a hydrogen atom, a halogen atom or a $C_1$–$C_{20}$-group, and two radicals $R^{20}$ or $R^{21}$ may form a monocyclic or polycyclic ring system which may in turn be substituted or unsubstituted, X is a halogen atom, Q is a heteroaryl which together with the cyclopentadienyl ring forms an azapentalene, thiopentalene or phosphapentalene which may in turn bear a group $R^{20}$ as substituent, l, l' are identical or different and are each an integer from zero to 4, B is a bridging structural element between the two cyclopentadienyl moieties.

12. A compound of the formula (IIa)

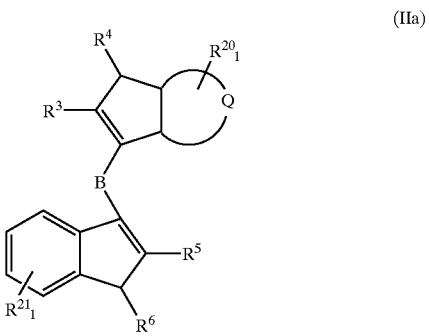

(IIa)

where
- M is Ti, Zr or Hf,
- $R^3$ is a $C_1$–$C_{20}$ group,
- $R^5$ is a hydrogen atom,
- $R^4$, $R^6$ are identical or different and are each a hydrogen atom or a $C_1$–$C_{20}$ group,
- $R^{20}$, $R^{21}$ are identical or different and are each a hydrogen atom, a halogen atom or a $C_1$–$C_{20}$ group, or two radicals $R^{20}$ or $R^{21}$ may form a monocyclic or polycyclic ring system which in turn may be substituted,
- X is a halogen atom,
- Q is a heteroaryl which together with the cyclopentadienyl ring forms an azapentalene, thiopentalene or phosphapentalene which may in turn bear a group $R^{20}$ as substituent,
- l, l' are identical or different and are each an integer from zero to 4,
- B is a bridging structural element between the two cyclopentadienyl moieties.

* * * * *

UNITED STATES PATENT AND TRADEMARK OFFICE
CERTIFICATE OF CORRECTION

PATENT NO.    : 6,627,764 B1
DATED         : September 30, 2003
INVENTOR(S)   : Schottek et al.

It is certified that error appears in the above-identified patent and that said Letters Patent is hereby corrected as shown below:

Column 37,
Line 46, "$R^{20} R^{21}$" should be -- $R^{20}$, $R^{21}$ --.
Line 63, "$C_1$-$C_{20}$group" should be -- $C_1$-$C_{20}$- group --.

Column 39,
Line 65, "claim 1" should be -- claim 4 --.

Column 40,
Line 1, "claim 1" should be -- claim 4 --.

Signed and Sealed this

Sixth Day of January, 2004

JAMES E. ROGAN
*Director of the United States Patent and Trademark Office*